(12) United States Patent
Bagwell et al.

(10) Patent No.: US 11,806,143 B2
(45) Date of Patent: Nov. 7, 2023

(54) LANCING DEVICE HAVING ANESTHETIC FEATURE

(71) Applicant: Actuated Medical, Inc., Bellefonte, PA (US)

(72) Inventors: Roger B Bagwell, Bellefonte, PA (US); Nicholas C Becker, Ebensburg, PA (US); Ryan S Clement, State College, PA (US); Brandon A Pier, State College, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 883 days.

(21) Appl. No.: 16/577,862

(22) Filed: Sep. 20, 2019

(65) Prior Publication Data

US 2020/0093410 A1 Mar. 26, 2020

Related U.S. Application Data

(60) Provisional application No. 62/734,433, filed on Sep. 21, 2018.

(51) Int. Cl.
*A61B 5/15* (2006.01)
*A61B 5/151* (2006.01)
*A61H 23/02* (2006.01)

(52) U.S. Cl.
CPC .... *A61B 5/150137* (2013.01); *A61B 5/15111* (2013.01); *A61B 5/150954* (2013.01);
(Continued)

(58) Field of Classification Search
CPC ........ A61B 5/150137; A61B 5/150954; A61B 5/15111; A61B 5/15113; A61B 5/15117;
(Continued)

(56) References Cited

U.S. PATENT DOCUMENTS 4,844,095 A 7/1989 Chiodo et al.
5,551,319 A 9/1996 Spaulding et al.
(Continued)

FOREIGN PATENT DOCUMENTS

EP 2243427 B1 4/2013
WO 2018170176 A1 9/2018

OTHER PUBLICATIONS

How DentalVibe Works. Retrieved from Internet, URL: DentalVibe.com/how-it-works/.
(Continued)

*Primary Examiner* — Philip R Wiest
*Assistant Examiner* — Nathan M Le
(74) *Attorney, Agent, or Firm* — METZ LEWIS BRODMAN MUST O'KEEFE LLC

(57) ABSTRACT

A handheld lancing device having anesthetic feature includes a housing removably retaining a disposable lancet. A carriage suspended within the housing by an isolation assembly may receive the lancet. A motor in mechanical communication with the lancet produces vibrations transmitted to contact surface, which vibrate a target lancing site prior to and during piercing. The target site is vibrated for a predetermined period of time before deploying the lancet. The isolation assembly permits movement of the carriage and/or lancet within the housing in one direction while limiting movement in other directions, and further dampens the vibrations of the motor from the housing held by the user. A force sensor detects force applied by the pressing of the contact surface against the skin of the patient. An indicator(s) perceivable to the user identifies when predefined positions of the lancet are reached for initiating vibration then triggering the lancet.

33 Claims, 15 Drawing Sheets

(52) U.S. Cl.
CPC ..... *A61H 23/02* (2013.01); *A61H 2201/0165* (2013.01); *A61H 2201/5061* (2013.01)

(58) Field of Classification Search
CPC ............ A61H 23/02; A61H 2201/5061; A61H 2201/0153
See application file for complete search history.

(56) References Cited

U.S. PATENT DOCUMENTS

| | | | |
|---|---|---|---|
| 5,984,940 A | 11/1999 | Davis | |
| 6,231,531 B1* | 5/2001 | Lum | A61B 5/150137 600/583 |
| 7,740,632 B2* | 6/2010 | Young | A61B 17/8822 606/92 |
| 8,043,229 B2 | 10/2011 | Mulvihill et al. | |
| 8,211,037 B2 | 7/2012 | Freeman et al. | |
| 8,328,738 B2 | 12/2012 | Frankhouser et al. | |
| 8,777,871 B2 | 7/2014 | Frankhouser et al. | |
| 8,777,944 B2 | 7/2014 | Frankhouser et al. | |
| 8,858,583 B2 | 10/2014 | Shtram | |
| 8,870,865 B2 | 10/2014 | Frankhouser et al. | |
| 8,992,439 B2 | 3/2015 | Mulvihill et al. | |
| 9,220,483 B2 | 12/2015 | Frankhouser et al. | |
| 9,770,561 B1* | 9/2017 | Dixon | A61M 5/422 |
| 2004/0215224 A1* | 10/2004 | Sakata | A61B 5/150503 606/181 |
| 2004/0254599 A1 | 12/2004 | Lipoma et al. | |
| 2005/0085839 A1* | 4/2005 | Allen | A61B 5/150068 606/181 |
| 2007/0060844 A1* | 3/2007 | Alvarez-Icaza | A61B 5/150954 600/583 |
| 2011/0077478 A1 | 3/2011 | Freeman | |
| 2011/0202012 A1 | 8/2011 | Bartlett | |
| 2012/0143086 A1* | 6/2012 | Jacobs | A61B 5/15186 600/583 |
| 2012/0283539 A1 | 11/2012 | Freeman | |
| 2013/0158586 A1* | 6/2013 | Pusey | A61B 5/150022 606/173 |
| 2013/0338537 A1* | 12/2013 | Pusey | A61B 5/15117 600/583 |
| 2014/0114250 A1* | 4/2014 | DeSalvo | A61M 5/2033 604/141 |
| 2015/0051630 A1* | 2/2015 | Cheng | A61B 5/150412 606/181 |
| 2015/0073357 A1 | 3/2015 | Bagwell et al. | |
| 2015/0141871 A1 | 5/2015 | Khast | |
| 2015/0157250 A1 | 6/2015 | O'Malley et al. | |
| 2018/0185606 A1* | 7/2018 | Van Schalkwyk | A61M 16/0816 |

OTHER PUBLICATIONS

McGinnis, K., et al., Effect of Vibration on Pain Response to Hell Lance, 2016 National Association of Neonatal Nurses, 2016, pp. 439-448, vol. 16, No. 6, National Association of Neonatal Nurses, Chicago, Illinois.

Baba, L., et al, The Efficacy of Mechanical Vibration Analgesia for Relief of Heel Stick Pain in Noeonates, J Perinat Neonat Nurs, 2010, vol. 24, No. 3, pp. 274-283, Wolters Kluwer Health/Lippincott Williams & Wilkins, Philadelphia, Pennsylvania.

Buzzy Drug Free Pain Relief, Buzzy Boot Camp, Retrieved from Internet, URL: https://buzzyhelps.com/pages-buzzy-boot-camp.

VibraJect Brochure, 2019, American Dental Association, 211 East Chicago Avenue, Chicago, IL 60611-2678.

Unistik 3 Brochure, Owen Mumford, Inc., 1755 West Oak Commons Court, Marietta, Georgia 30062.

International Searching Authority; International Search Report and Written Opinion of the International Searching Authority; International Application No. PCT/US19/52233; Patent Cooperation Treaty; pp. 1-14; publisher United States International Searching Authority; Published Alexandria, Virginia, US; copyright and dated Nov. 26, 2019; (14 pages).

International Searching Authority; International Search Report and Written Opinion of the International Searching Authority; International Application No. PCT/US22/37434; Patent Cooperation Treaty; pp. 1-11; publisher United States International Searching Authority; Published Alexandria, Virginia, US; copyright and dated Dec. 16, 2022; copy enclosed (11 pages).

* cited by examiner

LANCING DEVICE HAVING ANESTHETIC FEATURE

CROSS-REFERENCE TO RELATED APPLICATIONS

The present application claims the benefit of U.S. Provisional Application Ser. No. 62/734,433, filed on Sep. 21, 2018, the contents of which are incorporated herein by reference in its entirety.

STATEMENT REGARDING FEDERALLY SPONSORED RESEARCH OR DEVELOPMENT

This invention was made with government support under HD088139 awarded by the National Institutes of Health. The government has certain rights in the invention.

FIELD OF THE INVENTION

The present invention pertains generally to the field of medical devices, and more specifically to a device for making an incision, such as by lancing, while also providing a mechanically-induced anesthetic effect to the incision site before and during incision.

BACKGROUND

Blood collection is routinely necessary in the medical profession to assess, diagnose and monitor patient conditions and health. For example, blood samples are obtained from nearly every neonate born in the U.S. for numerous preventative screenings and diagnostic tests. The heel stick method, by which a sharp penetrates a superficial capillary bed of the foot to cause a small bleed, is the most common collection method. The procedure is considered moderate to severely painful, ranking in the top 25% by clinicians for common painful neonatal intensive care unit (NICU) procedures. It is conducted frequently, such as daily, during a NICU stay which can be weeks long. Studies also suggest that pain and stress responses caused by heel sticks are due to both the heel lance itself and by the post-lance heel squeezing for blood collection. Painful heel sticks may increase patient anxiety and fear of subsequent procedures, a side-effect of which is vasoconstriction which may impair blood collection. The immature pain system in preterm neonates has been characterized by hypersensitivity, overlapping receptive fields, prolonged windup periods, and immature descending inhibition. Additionally, there is a correlation between pain from heel sticks and free-radical generation, potentially risking exposure to oxidative stress. Together, these factors predispose neonates to a greater level of clinical and behavioral sequalae compared to older age groups.

These painful heel stick procedures occur during a critical developmental window previously associated with epochal brain development. Evidence suggests that exposure to repetitive painful experiences and analgesic drugs may cause excessive NMDA/excitatory amino acid activation, resulting in excitotoxic damage to developing neurons in neonates. This may alter pain sensitivity (e.g., hyperalgesia), and impact behavioral changes (e.g., increased anxiety, stress disorders, attention deficit disorder), and even potentially lead to impaired social skills and self-destructive behavior. Reducing neonatal pain and distress would therefore lead to long-term clinical improvements, such as by limiting neuronal excitotoxicity/apoptosis.

Clinical practice has evolved to address the need to reduce pain and improve heel stick efficacy. Today, it is essentially universally accepted that spring-loaded/automatic lancets are superior to manual techniques in terms of consistent performance, efficacy, pain, and safety. Clinicians have also explored numerous strategies to further reduce heel stick pain including pharmacological and non-pharmacological means, including oral sucrose, glucose, non-nutritive sucking, kangaroo care/skin-to skin contact, electrical stimulation, white noise, breastfeeding, music, and massage. Prolonged exposure to analgesic drugs has been implicated in permanent altering of the neuronal and synaptic organization of the neonatal brain and is thus less desirable. Non-pharmacological methods have shown varying levels of promise, with sucrose and non-nutritive sucking appearing to be some of the most effective and widely adopted strategies. Sucrose or pacifier usage is not always safe, such as for low gestational age (GA) infants, as it may lead to increases in short-term adverse effects, such as choking, oxygen desaturation, and bradycardia. Administration of sucrose may not be indicated for infants with unstable or high blood sugars. Furthermore, repeated doses of sucrose may put infants at risk for poorer neurodevelopment. Many other pain relief strategies are limited in terms of efficacy, practicality, available equipment, and disruption to normal practice. A solution is needed that provides drug-free reduction of the pain and stress responses from heel sticks and post-lance heel squeezing in neonates.

In NICUs and infant-mother nurseries, the current heel stick approach involves inserting a sharp lancet or blade into a neonate's heel, targeting a superficially capillary bed, followed by squeezing the heel causing blood to surface. Many current devices, such as those identified below, use a swinging motion that creates an incision through the capillary bed. Current newborn heel stick recommendations, based on postmortem and ultrasound studies, advise to perform the lance incision on the most medial or lateral portions of the plantar surface of the heel, not on the posterior curvature of the heel; to penetrate no deeper than 2.2 mm; and to avoid repeated incision through previous puncture sites that may be infected. These recommendations are in place to avoid calcaneal puncture and osteochondritis risk. Moreover, the capillary-rich beds in newborns are located at the dermal-subcutaneous junction between 0.35-1.6 mm below the skin surface, while pain fibers increase in abundance >2.4 mm below the skin surface.

Common heel lancing devices currently in use include the Tenderfoot®, Gentleheel®, QuikHeel™, Sterilance® Baby, TinyTouch™, and NeatlNick® lancets which use a single thrust activation to advance the sharp into the heel then retract, but do not provide anesthesia. The blades produce an incision that ranges in depth from 0.85-1.0 mm and width 1.75-2.50 mm, depending on product. The incision shape is relatively shallow to cause less pain but must be wide to transect many capillaries to collect sufficient blood volumes.

Vibration has also been used in some applications to attempt to mask the pain response. The concept draws on Melzack and Wall's Gate Theory of Pain, in which tactile stimulation masks the neural pain signals at the level of the spinal cord to produce a vibrational anesthesia effect. Vibrational anesthesia has proven effective for reducing pain associated with injections, such as local anesthetic injections, various dermatology procedures, eyelid surgery, venipuncture, intramuscular injections, and botulinum toxin injections.

Certain devices employ vibrational anesthesia in off-label use, such as the DentalVibe®, the Buzzy®, and various vibrational massage devices. For instance, the DentalVibe® is a dental tool having a pair of arms that are positioned on either side of an injection site. Once in contact with the patient's gums, the arms are vibrated, applying light vibration to the tissues around the injection site. Anesthesia injections are administered by a separate device while the tissue on either side of the injection is vibrated. Therefore, the DentalVibe® requires two-handed operation or two practitioners participating in the procedure—one to operate the DentalVibe® and one to perform the injection. It is also an injection, such as for Novocaine®, rather than lancing for blood collection.

Buzzy® is a device used in conjunction with injections, which combines cold and vibration to block out pain. Wings are frozen prior to use, then are attached to the device. Buzzy® is placed on the patient's skin, at the target injection site, with the frozen wings in direct contact with the skin. Buzzy® vibration is activated and held on the injection target site for 30-60 seconds, before being moved proximally in the direction of the head or spine for injection administration. Contact with the skin, and therefore application of cold and vibration, is maintained at the proximal site during injection administration to the pre-cooled/vibrated target injection site. Following injection administration, Buzzy® can be returned to the injection site to aid in post-delivery pain relief. However, while useful for injections delivering material, cold would be contraindicated for heel sticks, since cold is known to decrease blood flow which would inhibit blood collection from a heel lancing procedure.

Other devices externally add vibration to needles or syringes during injection delivery. For instance, the Vibra-Ject™ is a syringe attachment encompassing a vibrating motor that imparts non-directional vibration to the syringe. Similarly, Vibrovein™, is a micro-mechanical motor which attaches to commercial syringes and delivers a transverse vibration to the needle. However, neither of these devices have the means to deliver vibration-induced anesthesia prior to needle insertion, rather focusing on delivering vibration to the needle itself during needle insertion.

Therefore, a need exists in the medical industry for heel stick lancing devices that can reduce pain and trauma, in a non-pharmacological manner, while simultaneously providing sufficient blood flow for collection, preferably without having to squeeze the infant's foot further. Such a device could also be used for other lancing and quick stick procedures, not limited to infant heel sticks.

SUMMARY

The present invention is directed to a lancing device that combines vibration-induced anesthesia with a high-speed automatic lancet in a single handheld device that provides vibration-induced anesthesia to the lancing site prior to and during lancing procedure. Despite the vibration, it provides depth control for the lancing procedure, yielding high reliability and reproducibility of expected collection volumes. Therefore, the present device causes less pain and trauma responses without compromising blood sample quality or collection volume.

The device includes a housing, a lancet having a piercing member, and a contact surface disposed to contact the skin of the patient prior to and during lancing. The contact surface stimulates the skin at the target site to be lanced continually both before and during lancing procedure, masking neural pain signals at the level of the spinal cord, producing a vibration-induced anesthesia effect. Due to the pain inhibition potential of the device of the present invention, the piercing member of the lancet can penetrate slightly deeper, to about 1.8-2.0 mm target depth, and with a narrower incision, of about 1 mm, while yielding comparable blood volume to known automatic lancets. Because smaller cuts are produced, repeat is possible sampling when necessary.

A wide range of commercially available single use lancets may be inserted and retained in the housing of the present device during use, which can be removed or ejected following use. The housing may include a carriage that receives and retains the lancet in the device and maintains the alignment of the lancet with the opening of the housing through which the piercing member extends when deployed for incision. The carriage may be suspended within the housing or otherwise isolated from the housing walls by an isolation assembly. The distal end of the lancet includes a contact surface that is configured to contact the patient's skin when the lancet is in use. In some embodiments, the first end of the housing may include a contact surface configured to contact the patient's skin, rather than the lancet, when the device is in use.

A motor in mechanical communication with the tactile member(s) produces vibration when activated. Accordingly, the vibrations may be transferred through the lancet or a portion of the housing. These vibrations are transferred to the skin in contact with the tactile member(s) when the motor is activated. The concept draws on Melzack and Wall's Gate Theory of Pain, in which tactile stimulation masks the neural pain signals at the level of the spinal cord to produce a vibrational anesthesia effect. The motor is capable of delivering vibration with up to 0.5 mm displacement when the device is in contact with skin, producing a 50% reduction of lancet insertion force for the piercing member and consistent incisions for high reliability in collection.

An isolation assembly is disposed within the housing and is configured to dampen the vibrations between the motor and the portion of the housing held by a user or operator when in use. For instance, in some embodiments the isolation assembly may include springs such as those used to hold the carriage in suspension. In other embodiments it may be an elastomeric material disposed in a portion of the housing that absorbs vibration and restricts the vibration from the remainder of the housing. Regardless of location or type, the isolation assembly isolates the users' hand from the vibrations affecting the tactile member(s), providing greater comfort to the device operator. The handheld housing may also have an ergonomic shape for comfort.

The present invention therefore offers many improvements over known lancets. It minimizes pain and anxiety for patient and their loved ones. It improves outcomes by reducing distress associated with lancing procedures such as heel sticks. It is handheld and therefore easy to use. It can accommodate any lancet, which is preferably disposable for increased ease of use and hygiene. It can be used for any lancing or quick stick procedures for blood collection, such as but not limited to neonatal heel sticks, glucose testing, metabolic testing, allergy testing and others, and is particularly useful when repeated sticks to the same area are necessary.

The anesthetic lancing device, together with its particular features and advantages, will become more apparent from the following detailed description and with reference to the appended drawings.

DESCRIPTION OF THE DRAWINGS

Like reference numerals refer to like parts throughout the several views of the drawings.

DETAILED DESCRIPTION

Figure 1A:
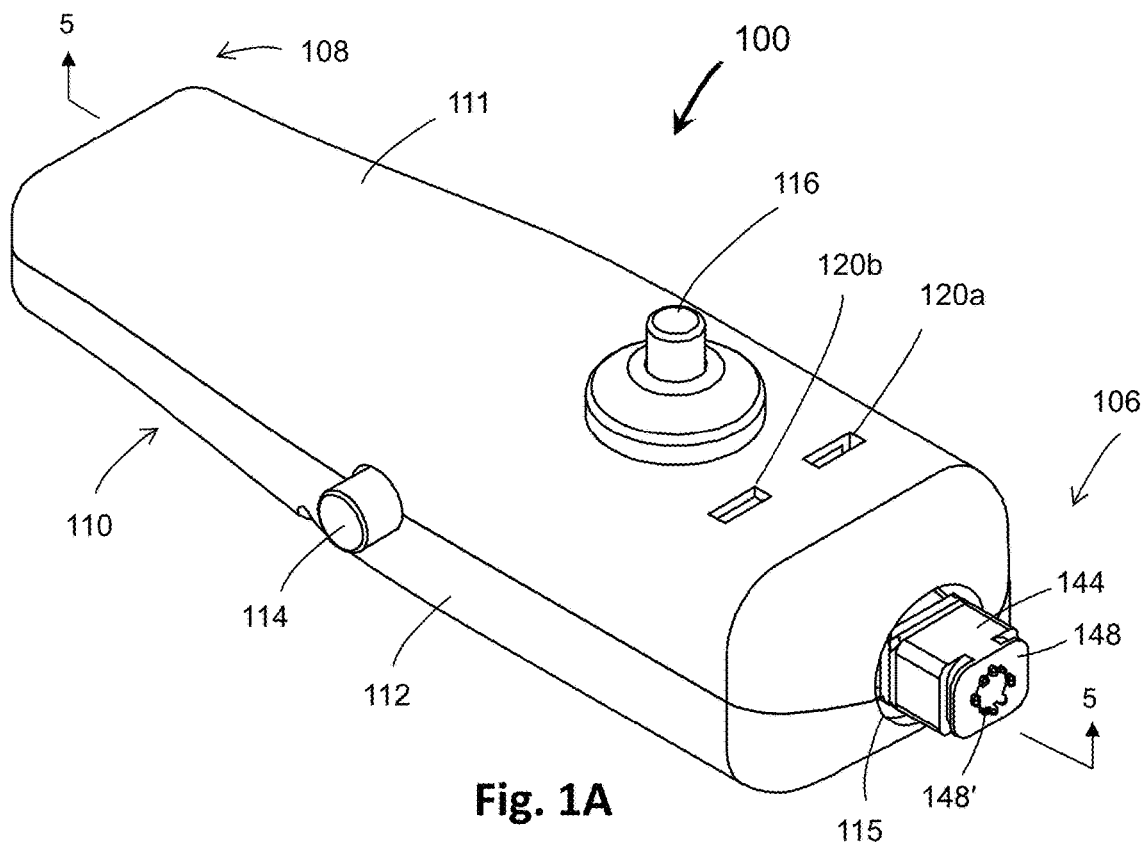
FIG. 1A is a top perspective view of one embodiment of the anesthetic lancing device of the present invention.

The present invention is directed to a vibration-inducing anesthetic lancing device 100 and its method of use. This device 100 is handheld and used to create an incision for subsequent blood draws, utilizing vibration for a drug-free reduction of pain and stress response from patients, for improved success rates and sample volumes. It thus provides many benefits to the collection of blood, particularly from neonates or other patients who may be subjected to multiple or repeated blood draws. The anesthetic lancing device 100 is preferably sized and dimensioned for single-handed use and may preferably have an ergonomic shape to facilitate ease of handling and operation.

As can be seen from FIGS. 1A-2B, the anesthetic lancing device 100 having a first end 106 and opposite second end 108. The device 100 is configured so the first end 106 may receive a lancet 140 and is positioned in proximity to the skin of a patient when the device 100 is in use. The second end 108 will therefore be closer to the user or operator of the device 100. The device 100 includes a housing 110, 110' which retains the other components of the device 100. The exterior of the housing 110, 110' provides an outer surface that can be comfortably held and operated by a user. The housing 110, 110' may be made of any suitable material, such as but not limited to biocompatible or medical grade plastic, ABS plastic, stainless steel, and other polymeric, plastic or metallic material or combinations thereof. The housing 110, 110' may be manufactured by any suitable method, including but not limited to deposition, subtractive rapid prototyping (SRP) milling, 3D printing, molding or other techniques. The housing 110, 110' is also sized and dimensioned to be held and operated by a single hand of the user. Further, in at least one embodiment the housing 110, 110' may be comprised of a top 111, 111' and bottom 112, 112' that correspondingly secure together to form a housing, and which may be selectively separated for access to the interior of the housing 110, 110' and its components when needed, such as for maintenance, repair or replacement of a part.

Figure 3:
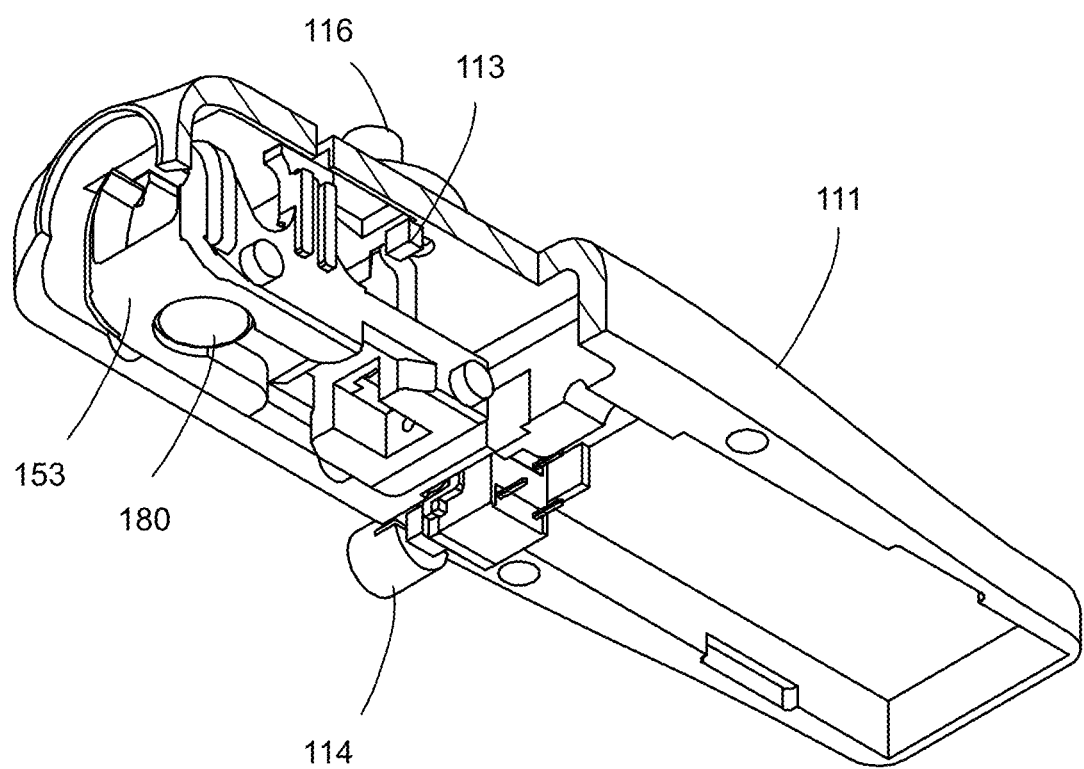
FIG. 3 is bottom perspective view of the inside of the housing top and underside of carriage, showing the restriction members.

In some embodiments, the housing 110 may also include at least one restriction member 113 extending into the interior space of the housing 110, as shown in FIG. 3. The restriction member(s) 113 may extend from the top 111 or bottom 112 of the housing 110, though preferably from the underside of the top 111 in at least one embodiment as shown in FIG. 3. The restriction member(s) 113 are positioned and have a length sufficient to limit or restrict the rotational movement of the lancet 140 within the housing 110. Thus, the restriction member(s) 113 keep the lancet 140 from twisting or rotating out of alignment when the cap of the lancet 140 is removed from the head 144, which typically occurs by twisting or rotating the cap to break its connection to the head 144. To accomplish this, the restriction member(s) 113 are configured to contact at least a portion of the lancet body 142 and/or carriage 150 into which the lancet 140 is inserted when a twisting motion would otherwise rotate the lancet 140, preventing further rotational movement in the direction of the torque being applied.

With reference to FIGS. 1A-5, the anesthetic lancing device 100 also includes a lancet 140 removably retained within the housing 110, 110'. Specifically, the lancet 140 may be a single-use lancet 140 that is inserted through an opening 115 in the housing 110, 110' and retained in the anesthetic lancing device 100 for use and then is removable from the device 100 after use for replacement by a fresh lancet 140. The lancet 140 may be any commercially available or proprietary lancet, such as but not limited to the safety lancet Unistik® 3-Neonatal (Owen Mumford Ltd., Oxfordshire, England) indicated for neonatal heel sticks. For instance, the lancet 140 may include a body 142 with a head 144 at one end and a piercing member 146 disposed therein. The body 142 may include a spring (not shown) that biases against and moves the piercing member 146 in the head 144 upon being deployed, as described in greater detail below.

The head 144 therefore also includes an opening with which the piercing member 146 is aligned and through which the piercing member 146 passes when deployed and retracted. The head 144 may be at least partially covered by a cap (not shown) when not in use, to protect the piercing member 146 from accidental sticks and maintain the sterility of the head 144. The cap may be removed from the head 144 such as by a twisting action once the lancet 140 is positioned within the anesthetic lancing device 100.

The device 100 further includes a contact surface 148 disposed at the first end 106 of the device 100 and configured to contact the skin of a patient when the device 100 is placed against the skin for use. The contact surface 148 is disposed on the lancet head 144 and/or housing 110 in proximity to and at least partially surrounding the opening 115 through which the piercing member 146 extends when deployed. Accordingly, the contact surface 148 is positionable at the target lancing site for piercing. As used herein, the terms "incision" and "lancing" may be used interchangeably. The contact surface 148 is configured to contact the patient skin and provide a vibrations to the lancing site that are perceived by the patient's brain, masking the sensation of the piercing member 146 when deployed and reducing the pain experienced by the patient.

Figure 1B:
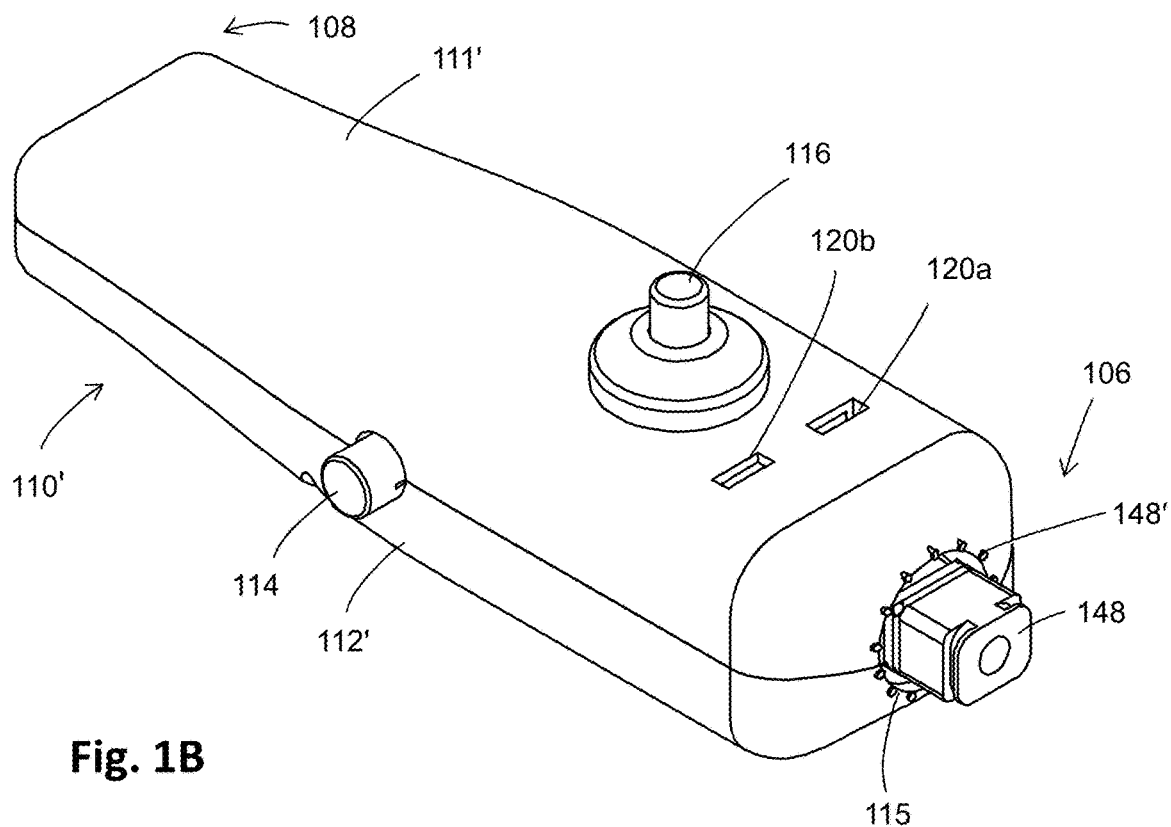
FIG. 1B is a top perspective view of a second embodiment of the anesthetic lancing device of the present invention.
Figure 1C:
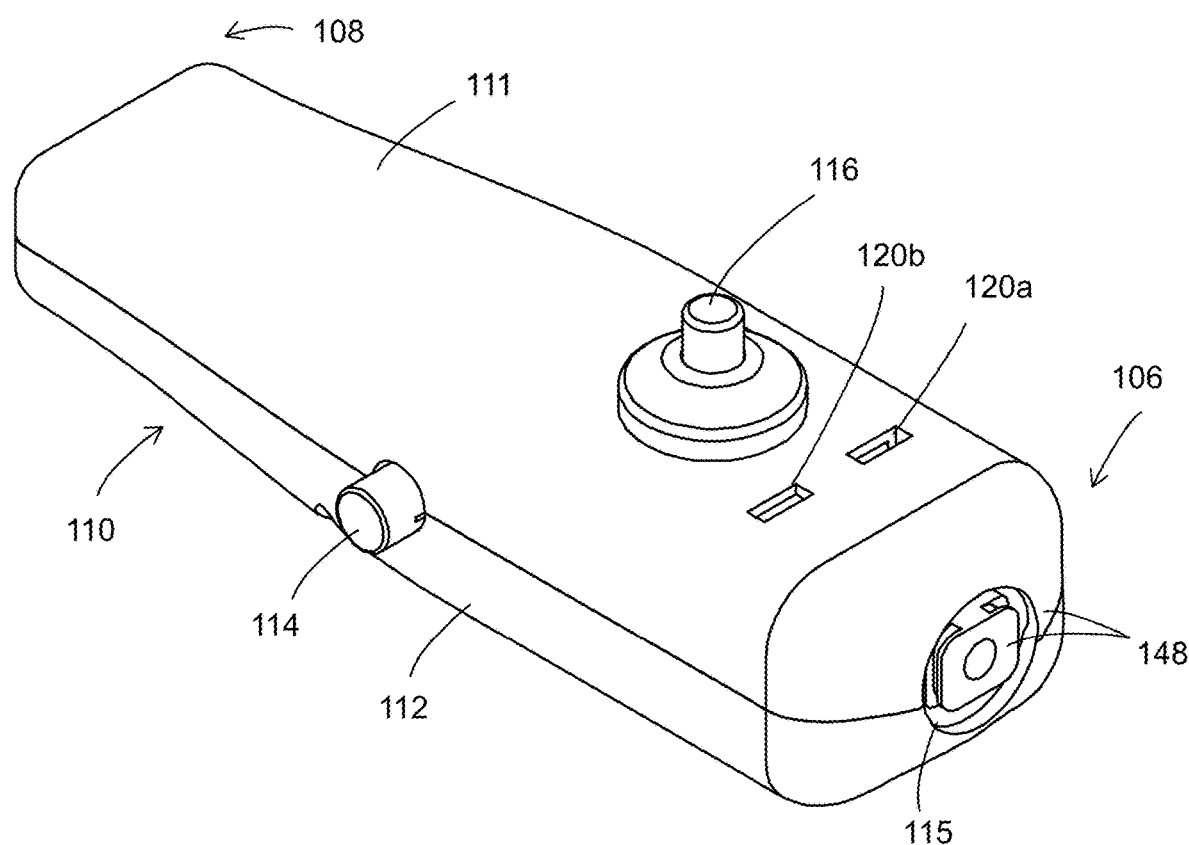
FIG. 1C is a top perspective view of a third embodiment of the anesthetic lancing device of the present invention.

In some embodiments, the contact surface 148 may be the distal end 145 of the lancet head 144, as shown in FIG. 1B. In other embodiments, the contact surface 148 may be located on the first end 106 of the housing 110, such as shown in FIG. 1C, such as when the lancet 140 is recessed within or flush with the housing 110 rather than extending therefrom. In some embodiments, such as when the lancet 140 is flush with the housing 110, the contact surface 148 may include both the distal end 145 of the lancet head 144 and the first end 106 of the housing, as in FIG. 1C. In certain embodiments, the contact surface 148 may include at least one tactile member 148', such as in FIGS. 1A, 2A, 4 and 5, which may extend from the head 144 of the lancet 140. One non-limiting example of such tactile member(s) 148 may be found in the UniStick® 3-Neonatal lancet (Owen Mumford Ltd., Oxfordshire, England). In other embodiments, such as shown in FIG. 1B, the tactile member(s) 148' may extend from the housing 110' at the first end 106, such as the top 111' and/or bottom 112' of the housing 110' rather than the lancet head 144'. When present, the tactile member(s) 148 may be of any shape, size and configuration, such as but not limited to beads, nubs, geometric shapes or patterns, linear or curvilinear and combinations thereof. For instance, in at least one embodiment the tactile member(s) 148 protrude about 0.5 mm from the surface of the head 144 and/or housing 110'. In some embodiments, the tactile member(s) 148 may provide friction between the device 100 and the skin of the patient to facilitate or enhance vibration.

Figure 5:
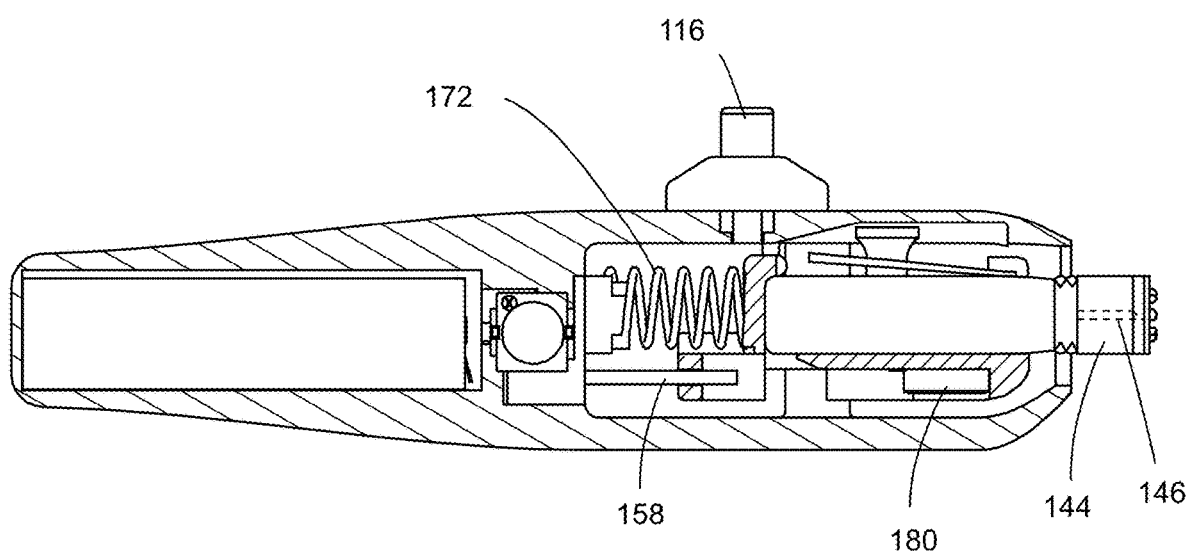
FIG. 5 is a cut-away side view of the interior of the anesthetic lancing device taken along line 5-5 from FIG. 1A.

As shown in FIG. 5, the piercing member 146 is affixed at the head 144 of the lancet 140. The piercing member 146 may be any sharps member suitable for lancing, such as but not limited to a needle, blade, or scalpel tip, and may be solid or hollow. For instance, in at least one embodiment, the piercing member 146 may be a solid needle having a gauge in the range of 18G to 30G and a diameter in the range of about 0.85 to 2 mm, though other gauges and diameters are also contemplated herein. In at least one preferred embodiment, the piercing member 146 may be a solid 18G needle with a 1 mm diameter. The gauge or diameter of the piercing member 146 determines the width of the incision. The piercing member 146 of the present device 100 therefore provides a narrower incision than other current heel stick methods, which create an incision shape that is relatively shallow for less pain but must be wide to transect sufficient capillaries for sufficient collection volume. The piercing member 146 is also configured to penetrate to a depth of no more than about 2-2.5 mm, preferably to a depth of about 1.8 mm. The piercing member 146 therefore goes deeper into the capillary-dense dermal-subcutaneous junction below the skin than other current lancet procedures for heel sticks, while still avoiding the increased density of dermal pain fibers that occur beyond 2.4 mm below the skin surface. Accordingly, the piercing member 146 in the present device 100 provides a narrower but deeper incision than current heel stick methods.

The piercing member 146 is preferably held within the head 144 in a retracted state when not deployed, such as prior to and following lancing. In the retracted state, the piercing member 146 does not extend beyond the surface of the head 144, as shown in FIG. 5. Therefore, the lancet 140 may be considered a "safety lancet" in which the piercing member 146 can only contact and pierce the skin when deployed, thus preventing accidental sticks for safety and hygiene reasons.

The lancet 140 also includes a lancet trigger 149 on the body 142. In at least one embodiment, the lancet trigger 149 may be a lever, button, or other structure on the exterior of the lancet 140 and which may be actuated to release the spring-loaded piercing member 146 and deploy the piercing member 146 through the opening 115 of the head 144 to make an incision or otherwise pierce the skin. The lancet 140 is preferably configured to automatically retract the piercing member 146 after deployment and store the piercing member 146 within the body 142, preferably preventing the piercing member 146 from leaving the body 142 again.

Figure 2A:
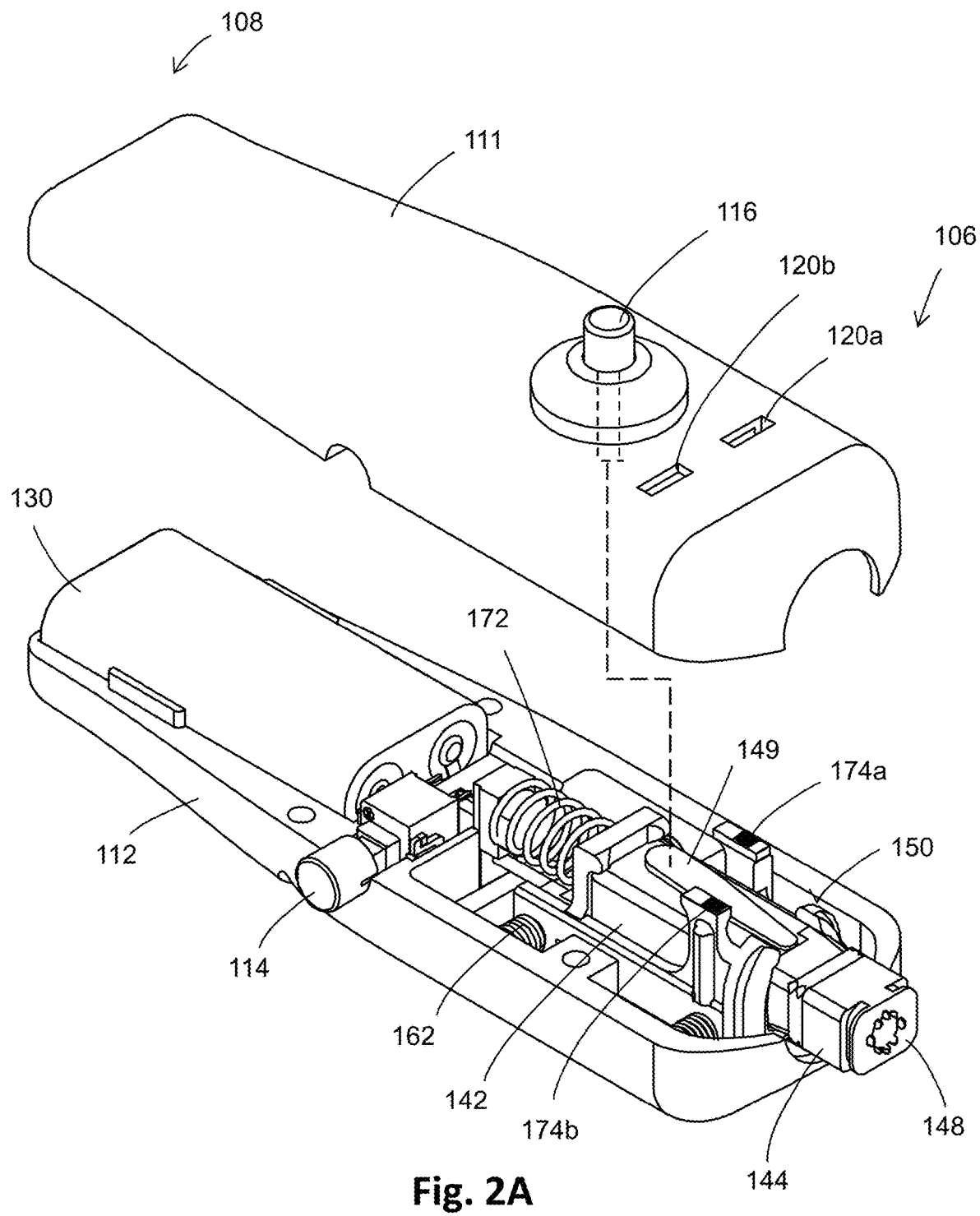
FIG. 2A is a partially exploded view of the housing of the anesthetic lancing device of FIG. 1A.
Figure 2B:
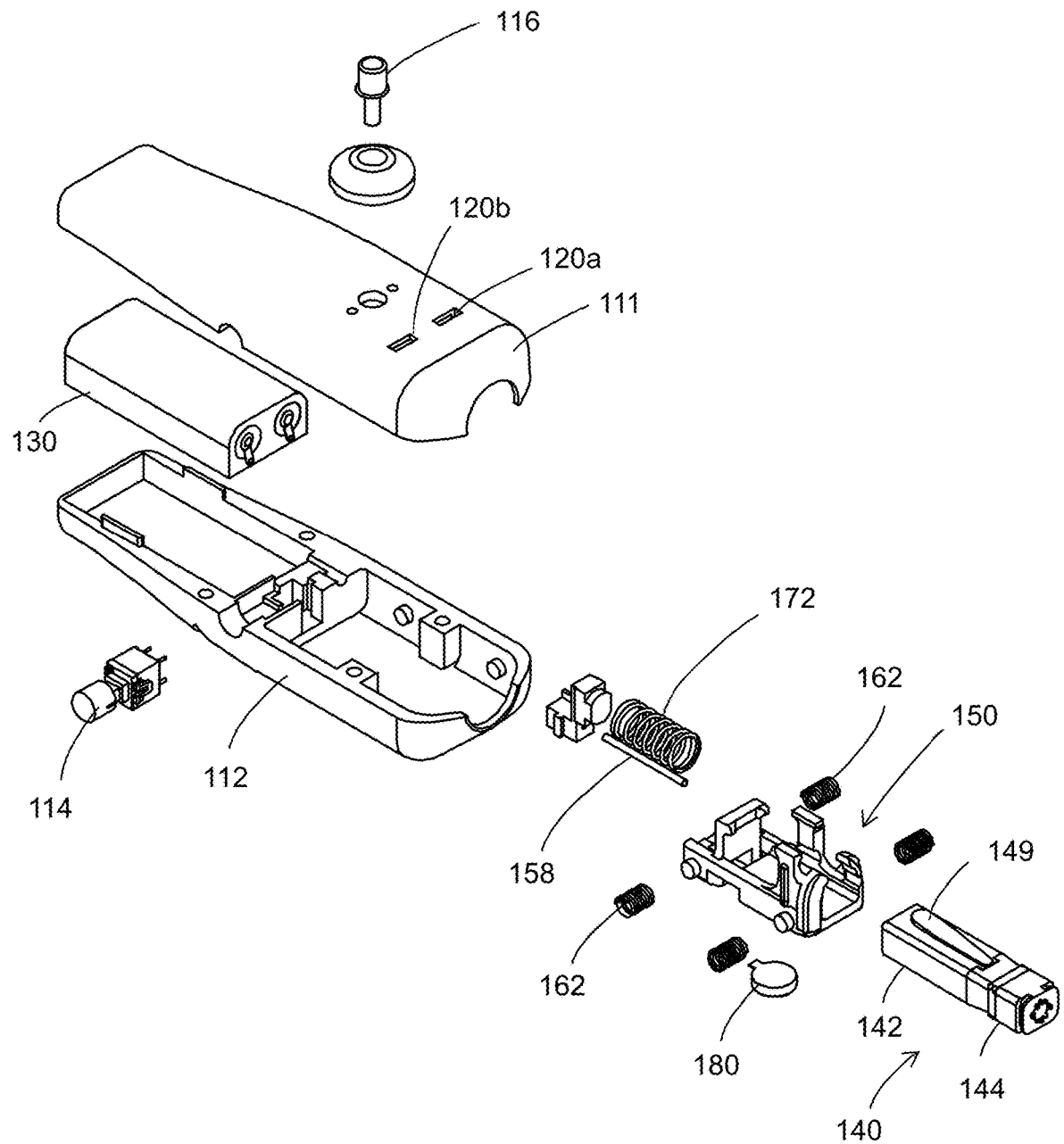
FIG. 2B is a fully exploded view of the interior components of the anesthetic lancing device of FIG. 2A.

With reference to FIG. 2A, the anesthetic lancing device 100 includes a trigger 116 that extends from the exterior surface of the housing 110. In at least one embodiment, the trigger 116 extends through the top 111 of the housing 110 and is aligned with the lancet trigger 149 of the lancet 140. A spring or other biasing member (not shown) may be included within the trigger 116 such that the trigger 116 is maintained in an up position. When a user presses down on the trigger 116 from the exterior of the device 100, the trigger 116 is depressed and contacts the lancet trigger 149, also depressing the lancet trigger 149 and causing the piercing member 146 to be deployed. Accordingly, the trigger 116 may be used to activate the lancet 140 within the device 100. The trigger 116 may be made of any material that will withstand the force necessary to depress it, such as but not limited to ABS plastic and stainless steel and may be made of medical grade or biocompatible materials.

The housing 110, 110' is configured to receive and retain the lancet 140 inserted therein for use. In at least one embodiment, such as shown in FIGS. 2A-7, the anesthetic lancing device 100 may also include a carriage 150 within the interior of the housing 110 that is specifically configured to receive and retain the lancet 140 within the device 100. The carriage 150, when present, may be used to properly seat and align the lancet 140 for use. To that end, the carriage 150 is located near the first end 106 of the device 100 in order to receive the lancet 140. The carriage 150 may be made of any suitable material, such as but not limited to ABS plastic, stainless steel, aluminum, or other material suitable for use in medical devices. The carriage 150 may be made of the same or different material as the housing 110, 110' or the lancet 140.

Figure 6:
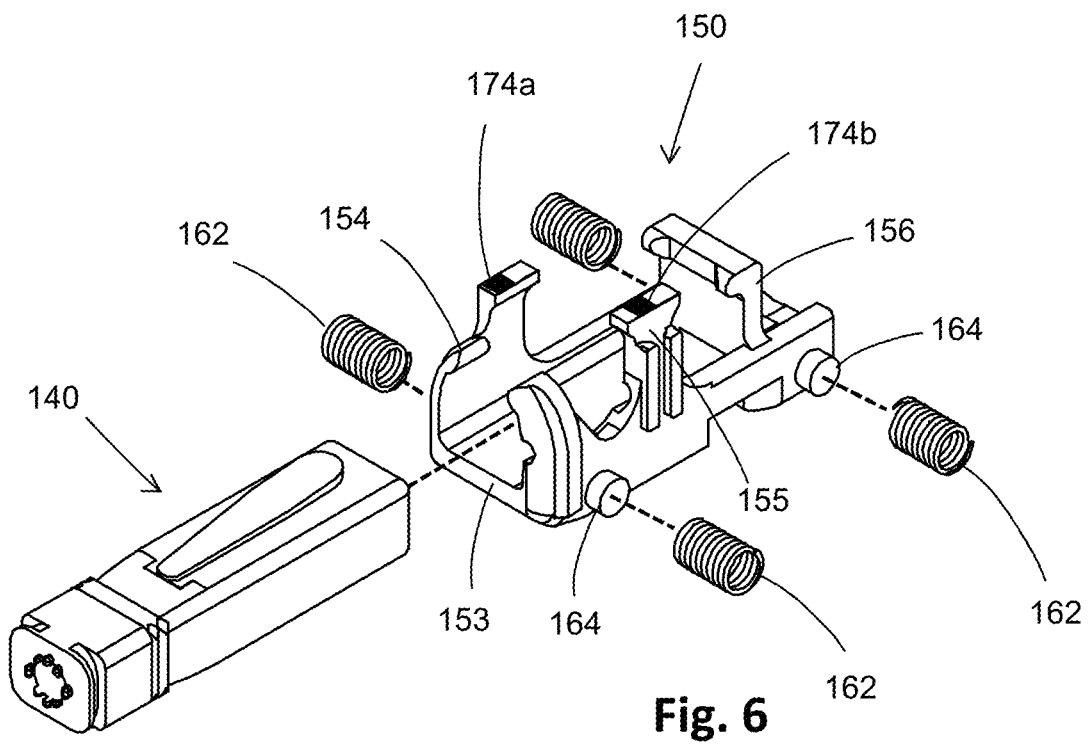
FIG. 6 is a front perspective exploded view of one embodiment of the lancet and carriage of the anesthetic lancing device.
Figure 7:
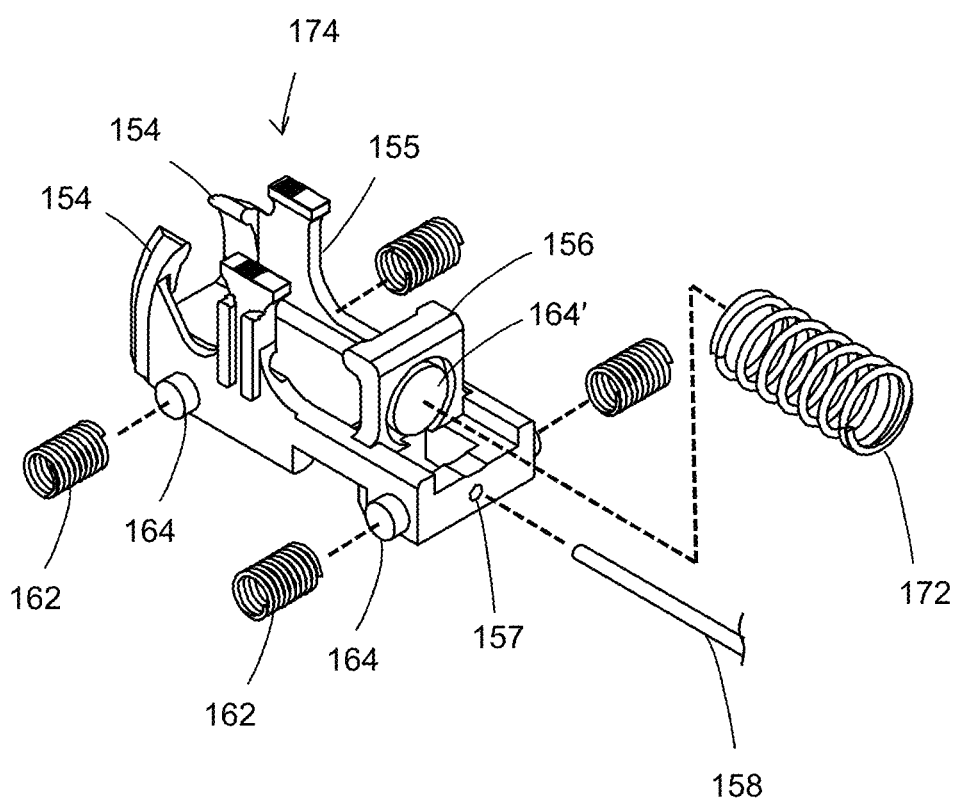
FIG. 7 is a back perspective exploded view of the carriage and pressure spring of the anesthetic lancing device of FIG. 6.

The carriage 150 may include a bottom 153 on which a portion of the lancet 140, such as the body 142, rests when inserted. The carriage 150 also includes at least one guide member 155 that is positioned to guide the lancet 140 into the housing 110 in proper alignment. In at least one embodiment, as shown in FIGS. 2A-7, the carriage 150 includes a pair of guide members 155 disposed on either side of the bottom 153 and which act as barriers to restrict lateral movement of the lancet body 142, thereby centering the lancet 140 in the housing 110, 110'. The guide members 155 may extend from the bottom 153 of the carriage 150 and may extend to the underside of the top 111 of the housing 110, 110' in at least one embodiment. The carriage 150 also includes a back plate 156 which is positioned to receive the rearward terminal end of the lancet body 142 that is opposite the head 144. The back plate 156 is therefore disposed at the end of the carriage 150 furthest from the first end 106 of the housing 110, 110' and opening 115 through which the lancet 140 is inserted. The carriage 150 may also include at least one, but preferably a plurality of retention members 154 configured to removably retain the lancet 140 within the carriage 150 once inserted. The retention members 154 may cooperatively work to retain the lancet 140 within the carriage 150. For instance, the retention members 154 may have a frictional fit against a portion of the lancet 140. In at least one embodiment, the retention members 154 may be made of a resilient material such as but not limited to ABS or any other polymers with sufficient yield strength so they may be temporarily flexed, deflected or deformed to accommodate the passing of the lancet 140. They may also be spring-biased or otherwise biased against the lancet 140 such that the lancet 140 pushes against the retention members 154 during insertion into the housing 110, 110' and the retention members 154 may push back against the lancet 140 when it is positioned within the carriage 150. When the lancet 140 is selectively removed from the housing 110, 110' after use, the retention members 154 may return to their resting conformation. The retention members 154 may be disposed anywhere along the carriage 150 to facilitate the maintenance of the lancet 140 in position, such as but not limited to on either side of the carriage 150, and therefore lancet 140, such as shown in FIGS. 2A, 6 and 7.

The carriage 150 is mounted within the interior of the housing 110, 110'. In some embodiments, the carriage 150 may be directly affixed to the inner surface of either the top 111 or bottom 112 of the housing 110, 110'. In a preferred embodiment, however, the carriage 150 is movably mounted to the housing 110, 110' through an isolation assembly 160. The isolation assembly 160 is configured to connect the carriage 150 to the housing 110, 110' in a way that permits the vibration or movement of the carriage 150 but insulates this movement or vibration from being transmitted to the housing 110, 110', and thus to the hand of the user.

In at least one embodiment, as shown in FIGS. 2A-7, the isolation assembly 160 may include at least one, but preferably a plurality of isolation members 162 disposed between and connecting the carriage 150 to the housing 110, 110'. As shown in this embodiment, the isolation members 162 may be springs having a sufficient length and spring constant to suspend the carriage 150 within the interior space of the anesthetic lancing device 100 so the carriage 150 does not contact the housing 110, 110' but is also sufficiently flexible to absorb the vibrations and movements of the carriage 150. For example, the spring isolation members 162 may have a length in the range of 5 to 20 mm and preferably about 10 mm and may have a spring constant in the range of 25 to 100 N/m and preferably about 50 N/m. There may be any number of isolation members 162 between the carriage 150 and the housing 110, 110', such as but not limited to two, three, four, six or eight. In the embodiment shown in FIGS. 2A-7, there are four such isolation members 162, one near each corner of the carriage 150. In other embodiments, the isolation member 162 may be a barrier made of vibration absorbing material at least partially surrounding the carriage 150 and/or lancet 140. For instance, materials such as but not limited to potting material, low durometer silicone such as NuSil™ MED 2-4013 fast cure silicone adhesive (NuSil Technology LLC, Carpinteria, Calif.), or any polymeric material with some elasticity for absorbing vibration may be used as the isolation member 162 when acting as a barrier.

Figure 8:
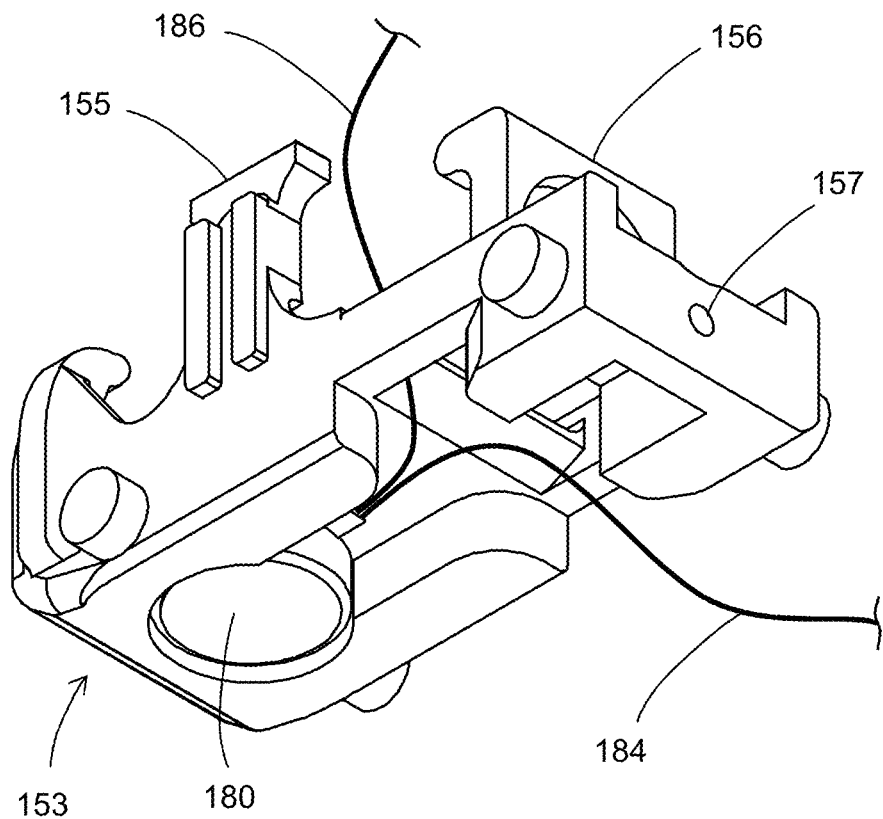
FIG. 8 is a bottom perspective view of one embodiment of the carriage and motor of the anesthetic lancing device.

The carriage 150 may also include at least one connection point 164 where the corresponding isolation member 162 contacts and/or connects to the carriage 150. The connection point(s) 164 may be co-extensive with the surface of the carriage 150 or may be recessed in or extending from the surface of the carriage 150. In the embodiment shown in FIGS. 6-8, the connection points 164 are nubs, knobs, or other extensions that protrude from the surface of the carriage 150, such as the side surface of the carriage 150. They may have any shape, size or configuration. As shown in FIGS. 6-8, the connection points 164 may be sized to receive the corresponding isolation member 162, such that the connection point 164 fits within the inner diameter of the isolation member 162. Thus, the connection point 164 may help hold up the carriage 150. The isolation member 162 may be affixed or secured to the connection point 164 at one end and the housing 110, 110' at the other end and may be releasably secured or permanently secured. In at least one embodiment, the isolation member 162 is permanently secured to the connection point 164, such as by adhesive, bonding, welding or other similar method of secure attachment.

Figure 4:
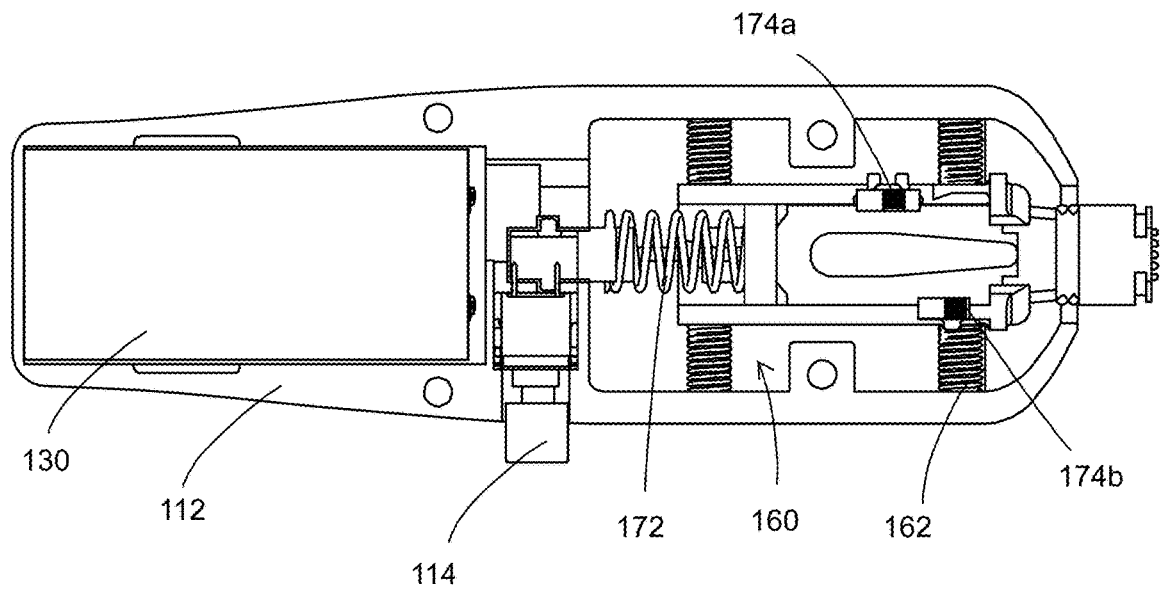
FIG. 4 is a top plan view of the interior of one embodiment of the anesthetic lancing device.

The device 100 may also include at least one alignment member 158 configured to maintain the carriage 150 in alignment within the housing 110, 110'. For instance, as shown in FIGS. 4, 5 and 7, an alignment member 158 may extend from a portion of the housing 110 into the interior space where the carriage 150 is located. The back of the carriage 150 may include an aperture 157 through which the alignment member 158 is received. The aperture 157 is therefore at least as large as the alignment member 158 and may be large enough that the carriage 150 can move relative to the alignment member 158 in one direction, such as along the length of the alignment member 158 but is restricted from much movement in other directions. For instance, in the embodiments of FIGS. 2A-7 and as best depicted in FIG. 5, the carriage 150 may be movable along the length of the alignment member 158 in an axial direction that is in line with or parallel to the axial direction of the lancet 140 and the piercing member 146 thereof. However, the alignment member 158 limits movement of the carriage 150 along a vertical axis, such as upward in the direction toward the top 111 of the housing 110 or downward in the direction toward the bottom 112 of the housing 110. This may be particularly useful in embodiments in which the carriage 150 is suspended within the interior space of the housing 110 by an isolation assembly 160 since the isolation members 162 would permit movement in any direction, including along the vertical axis as described above, depending on the elasticity or spring constant of the isolation members 162. For instance, when the user presses down on the trigger 116, it contacts and presses down on the lancet trigger 149, as described above. This pressure also forces the entire lancet 140 down, along with the carriage 150 in which it resides, since the carriage 150 is elastically suspended. The isolation members 162 would flex or stretch in response to such downward pressure, allowing the entire carriage 150 and lancet 140 to be moved downwardly toward the housing 110, rather than triggering the lancet trigger 149. However, the alignment member 158 extending through the aperture 157 of the carriage 150 limits movement of the carriage 150 in the downward direction as limited by the size of the aperture 157. This prevents the carriage 150 from being pushed into the bottom 112 of the housing 110 and ensures that the lancet trigger 149 will be activated. It also maintains the suspended positioning of the carriage 150 and the alignment of the lancet head 144 relative to the opening in the housing 110 so the piercing member 146 may extend through the housing 110 upon the lancet 140 being triggered.

The anesthetic lancing device 100 also includes a force indicating system which senses the amount of force applied to the lancet 140 from contact with the patient's skin and may indicate to the user when sufficient force has been achieved to begin vibration and/or triggering the lancet 140 for piercing. This may be helpful since a certain amount of skin contact is necessary to achieve the pain masking ability of the vibration of the anesthetic lancing device 100. If too little contact or force is achieved, the patient will not sufficiently feel the vibration at the target incision or lancing site and the pain sensation may be not sufficiently masked. If too much force is applied, the vibrations from the device 100 may be dampened which would decrease the anesthetic effect. Therefore, the force indicating system allows a user to achieve the optimal results for pain masking. It also provides a method of using the anesthetic lancing device 100 to achieve more uniform results, both from the same user over different lancing procedures and between different users. Current lancet operation requires the user to apply their own judgment on how to hold and press the lancet against the skin for operation, which leads to variability in results. The present anesthetic lancing device 100 avoids this variability and provides more uniformity, allowing busy medical staff and even non-medically trained individuals to perform lancing procedures efficiently and consistently.

The force indicating system may be a mechanical or electrical system that registers or detects force applied to the lancet 140 from pressing the device 100 on the target site and reports this information to the user for operating the device 100. The force indicating system includes at least one force sensor 172 configured to detect, measure and/or respond to force applied to the lancet 140. For instance, in at least one embodiment such as shown in FIGS. 2A-5 and 7, the force sensor 172 may be a spring or other elastomeric structure biased against the lancet 140 within the housing 110, preferably axially in line with the lancet 140. Specifically, the force sensor 172 spring may contact and be biased against a portion of the carriage 150, such as the back plate 156 of the carriage 150. A connection point 164' along the back plate 156 of the carriage 150, as shown in FIG. 7, may be configured to receive and/or contact the force sensor 172 spring such that the force sensor 172 spring is preferably in line axially with the lancet 140 when positioned within the carriage 150. The opposite end of the force sensor 172 spring may be secured to a portion of the housing 110, such as the bottom 112. In other embodiments, the force sensor 172 may be an electronic pressure detector positioned anywhere in contact with the lancet 140, housing 110 and/or carriage 150.

When the operator or user contacts the lancet 140 with the skin of the patient at the target lancing site and applies pressure, the lancet 140 will be pushed further into the housing 110 toward the second end 108 along the longitudinal axis of the lancet 140. The carriage 150 will also move with lancet 140 since the lancet 140 is secured therein and the carriage 150 is movable relative to the housing 110. The force sensor 172 detects the amount of pressure or force applied by the lancet 140, such as by the force sensor 172 spring compressing between the lancet 140 and/or carriage 150 and the housing 110. As the lancet 140 and/or carriage 150 moves rearwardly in the direction of the second end 108 of the housing 110, the force sensor 172 spring increases in compression and the carriage 150 moves axially along the alignment member 158, which ensures the carriage 150 does not deviate too far laterally to either side and the piercing member 146 remains aligned with the opening 145 in the housing 110.

The pressure indicating system 170 also includes at least one, but preferably a plurality of indicators 174 presented to or perceivable by the user that provide information on the force applied to the lancet 140 based on information from the force sensor 172. The indicators 174 therefore assist the user in operating the anesthetic lancing device 100. These indicators 174 may be mechanical or electrical in nature. For instance, in at least one embodiment as shown in FIG. 7, the indicators 174 may be indicia on a portion of the carriage 150 that indicates certain force currently being applied to the lancet 140. The indicia may be any suitable indicia, such as but not limited to markings, colorings, icons, geometric patterns, letters, numbers and other mechanical markings. In other embodiments, the indicators 174 may be electrical such as but not limited to lights, such as LEDs, which may be colored or white light and may be present in different colors or change in intensity, blink or flash to provide information on pressure as detected by the force sensor 172. Regardless of type, the indicator(s) 174 may be viewable or otherwise perceivable to the user during operation. For instance, in at least one embodiment, the indicator(s) 174 may be viewable to a user through a window in the housing 110, 110', such as in the top 111, 111' of the housing 110, 110' as shown in FIGS. 1A-2B, 10B and 11B. In other embodiments, the indicator(s) 174 may be present on the sides of the housing 110, 110', such as when they are lights. In still other embodiments, the indicator(s) 174 may be vibrations, such as pulses, emitted by the device when certain predefined pressure thresholds are reached and which may be detected by the user through tactile sensations in the hand that grips the device 100. In still further embodiments, the indicator(s) 174 may be a sound emitted be a speaker associated with the force sensor 172 configured to produce a sound when certain predefined pressure thresholds are reached. Such sounds may be beeps, alarms, chimes, or other audibly detectable noises. The indicator(s) 174 may include any combination of the above.

In at least one embodiment, as shown in FIGS. 2A-5, 7 and 10A-11B, the indicators 174 may be mechanical markings on a portion of the carriage 150. There may be different indicators 174 each representing a different specific pressure range or value. For instance, a first indicator 174*a* may be positioned along the carriage 150 to indicate a first pressure and a second indicator 174*b* may be positioned to indicate a second pressure which is greater than the first pressure. In the embodiment of FIGS. 2A-5, 7 and 10A-11B, the first and second indicators 174*a*, 174*b* may be located at terminal ends of the guide members 155 of the carriage 150 which are disposed in proximity to the underside of the top 111 of the housing 110 such that they are configured to align with and be visible through corresponding first and second indicator windows 120*a*, 120*b*, respectively, of the top 111 of the housing 110 when certain corresponding pressures are sensed by the force sensor 172. Accordingly, the first and second indicators 174*a*, 174*b* may be located along different portions of the carriage 150 such that different ones of the indicators 174a, 174b are presented and viewable through the indicator windows 120a, 120b when the corresponding pressure is sensed. In certain embodiments, there may be a single indicator window through which the various indicators 174a, 174b are viewable when the corresponding pressure is sensed. Thus, the indicators 174a, 174b may be positioned at different locations of the same portion of the carriage 150, such as along the same guide member 155. In other embodiments, such as shown in FIGS. 2A-5, 7 and 10A-11B, the indicators 174a, 174b may be located on different guide members 155 and are viewable through dedicated indicator windows 120a, 120b, respectively, of the housing top 111.

Figure 10A:
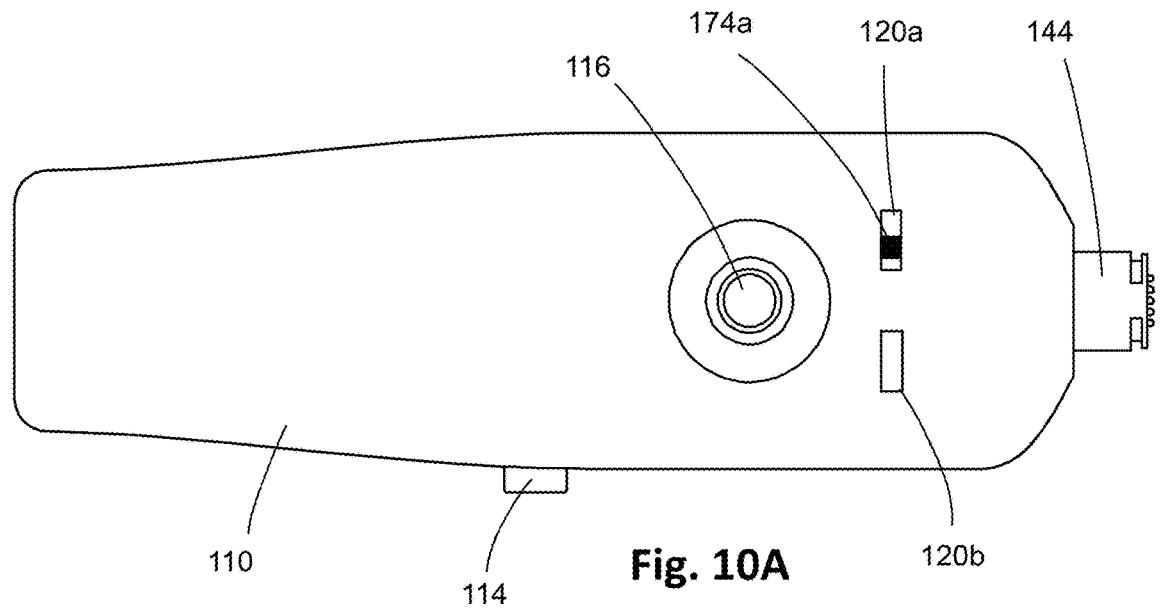
FIG. 10A is a top plan view of one embodiment of the of the interior of the anesthetic lancing device with the carriage in a first compressed position, ready for the application of vibration.

In at least one embodiment such as shown in FIGS. 2A-5, 7 and 10A-11B, the first indicator 174a is indicative of a first force range or value that is predetermined to be optimal for beginning vibration of the anesthetic lancing device 100. In use, when a user operating the device 100 first contacts the patient at the target lancing site with the device 100, such as with the head 144 of the lancet 140 secured therein, there is minimal force detected by the force sensor 172. As the user pushes the device 100 against the patient, the force increases, pushing the lancet 140 and therefore carriage 150 increasingly rearwardly and compressing the force sensor 172 spring. At a certain point, sufficient force will have been applied to bring the first indicator 174a into alignment with the first indicator window 120a such that the user may then see the first indicator 174a through the first indicator window 120a. This positioning tells the user that sufficient force has been detected that vibration of the device 100 can be initiated, as described below. This corresponds to a pressure that allows the vibration to be detected by the patient to mask the pain response. For instance, in at least one embodiment the first indicator 174a corresponds to a force in the range of about 0.001 to 10 N and preferably about 1 N. This may be referred to as a first position of the lancet 140 and/or carriage 150, such as shown in FIGS. 10A-10B.

Figure 11A:
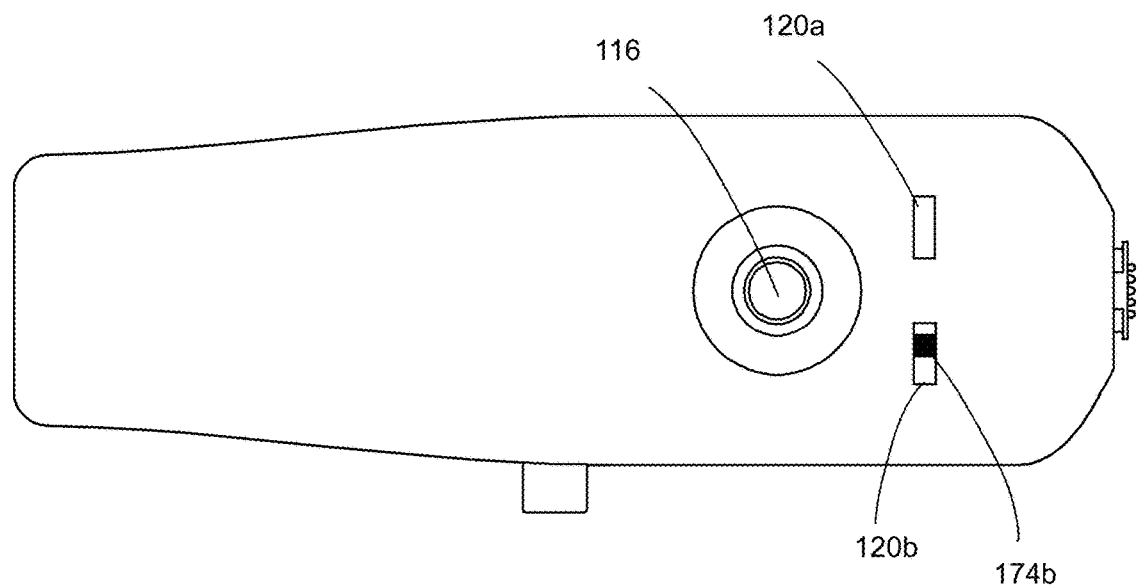
FIG. 11A is a top plan view of the one embodiment of interior of the anesthetic lancing device with the carriage in a second compressed position, ready for triggering the lancet.
Figure 11B:
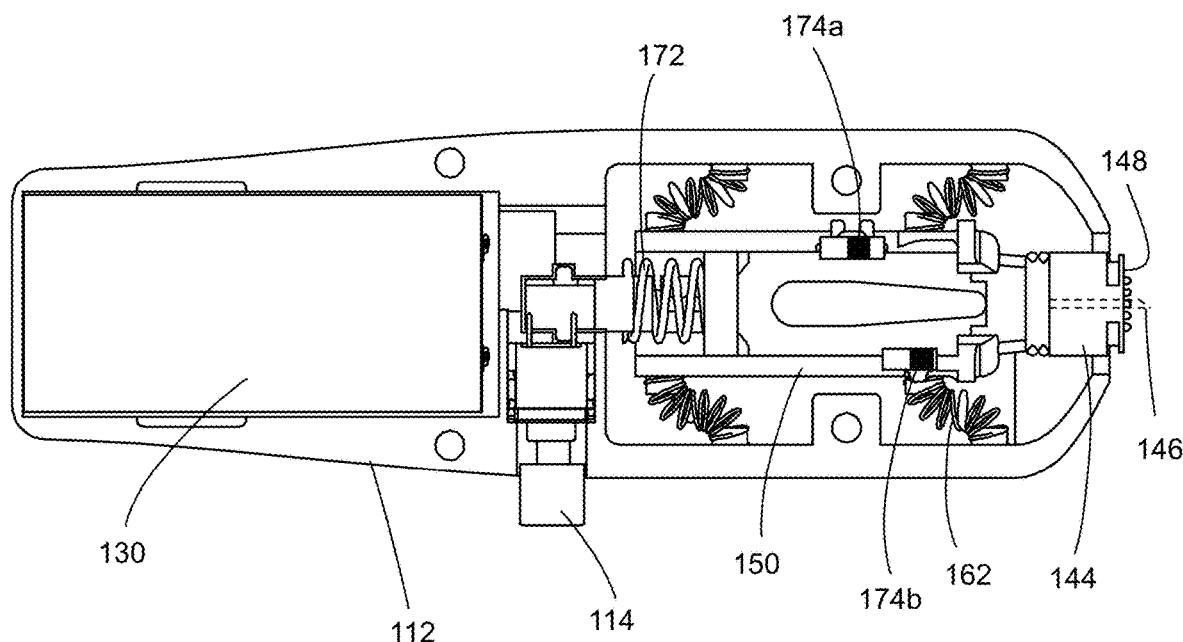
FIG. 11B is a top plan view of the exterior of the anesthetic lancing device of FIG. 11A.

The user may continue pressing the device 100 further against the target site once vibration has commenced. This applies increasing force to the lancet 140, carriage 150 and force sensor 172 and further moves the lancet 140 and carriage 150 in a rearward direction toward the second end 108 of the housing 110. At a certain point, the second indicator 174b becomes aligned with and may be viewable through the second indicator window 120b in the housing top 111. When the second indicator 174b is viewable, a second force has been detected by the force sensor 172. This second force is therefore a higher or greater amount of force than the first force indicated by the first indicator 174a. The second indicator 174b is indicative of a force at which the device 100 may be triggered to release or deploy the piercing member 146 for lancing or incising the skin of the patient at the target lancing site, and which will provide a sufficiently deep incision to achieve sufficient volume of blood collection but is also a low enough pressure that the incision will avoid the piercing member 146 reaching the nerve-dense portion of the dura. For instance, the second force may be in a range of about 2 to 10 N and preferably about 3 N. This may be referred to as a second position of the lancet 140 and/or carriage 150, such as shown in FIGS. 11A-11B.

Any number of indicators 174 may be provided, each representing a different pressure or pressure range at which actions can be taken, such as but not limited to starting vibration, stopping vibration, actuating the trigger 116 to deploy the piercing member 146 and others. The force sensor 172 and indicator 174 placement may therefore be selected and/or calibrated to the desired pressures or pressure ranges for respective activities desired. In certain embodiments, such as in electrical pressure indicating systems 170, the device 100 may be configured such that only certain actions may be taken when certain pressures are indicated by the force sensor 172 and/or indicators 174. For instance, an electrical circuit may remain open until the second pressure is achieved and the second indicator 174b is activated, at which point the circuit may be closed. This would prevent the trigger 116 from being actuated and the piercing member 146 from being deployed before sufficient pressure is achieved, thus ensuring a sufficient amount of time has elapsed for vibration to produce an anesthetizing effect and/or that proper depth will be reached. Similarly, the circuit may be again opened once too much pressure is achieved, thereby preventing the triggering of the piercing member 146 when it would be deployed too deep within the skin of the patient, thereby avoiding the nerve-dense area of the skin. In mechanical embodiments, a blocking member may restrict contact between the trigger 116 and lancet trigger 149 until the second pressure is sensed or detected by the force sensor 172, achieving the same result. In other embodiments, however, the indicators 174 may be useful to a user but not required for operation of the device 100, such that a user or operator may have the freedom to use the device 100 at whatever pressure they see fit.

The anesthetic lancing device 100 also includes a motor 180 that is configured to produce vibrations when activated which are then transferred to the contact surface 148. The motor 180 may be any suitable motor for a handheld device, such as but not limited to a disc motor, DC motor, off-balance DC motor, piezoelectric motor or other type motor. For instance, in at least one embodiment the motor 180 may be a disc motor rated for up to 12,000 rpm at 3 $V_{DC}$, preferably operative at about 10,000 rpm, and may have a diameter up to 10 mm but more preferably up to about 1 mm and still more preferably about 0.4 mm. In at least one other embodiment, the motor 180 may be a DC motor operative to produce vibrations sufficient to vibrate the contact surface 148 at a frequency in the range of 50-500 Hz, preferably in the range of about 140-200 Hz, and still more preferably about 150 Hz.

The motor 180 is affixed to the housing 110 or carriage 150 in mechanical communication with the lancet 140. For example, in at least one embodiment as shown in FIGS. 5 and 8, the motor 180 may be secured underneath the carriage 150 near the first end 106 of the device 100, such as to the underside of the bottom 153 of the carriage 150 on the opposite side of the same surface on which the lancet 140 rests in the device 100. Accordingly, vibrations produced by the motor 180 are transmitted through the bottom 153 of the carriage 150 and to the lancet 140, thereby vibrating the contact surface 148 on the head 144 of the lancet 140 accordingly. In other embodiments, the motor 180 may be mounted within the housing 110 at the first or second end 106, 108 of the device 100 to a portion of the housing 110 such that vibrations are transmitted to the contact surface 148 regardless of whether it is located on the head 144 of the lancet 140 or on the first end 106 of the housing 110. In such embodiments, an isolation member 162 such as a barrier may be disposed at least partially around the portion of the housing 110 where the motor 180 is mounted, to dampen the vibrations felt by the user or operator while not dampening the vibrations transmitted to the lancet 140 or first end 106 of the housing 110. Regardless of where the motor 180 is mounted, it may be secured to the housing 110 or carriage 150 by any suitable method, such as but not limited to adhesive, bonding, screws, and other secure fasteners.

The motor 180 is configured to produce vibrations when turned on or activated. Preferably, this vibration may be multi-directional vibration that is not specific to any axis or direction, though in certain embodiments the vibrations may be directed along a particular axis, such as in line with, co-extensive or parallel to the longitudinal axis of the lancet 140 and therefore the piercing member 146. A scotch-yoke mechanism, swashplate or other similar mechanism may be used to convert rotational motion of the motor 180 to an axial motion for a specific directional vibration or oscillation. As used herein, the terms "vibrate" and "oscillate" may be used interchangeably.

The motor 180 is configured to produce vibrations that, when transmitted, will cause the contact surface 148 to vibrate or oscillate at a displacement in the range of up to 1 mm, preferably about 0.5 mm. As noted previously, this vibration or oscillation may be omni-directional, laterally (side-to-side), longitudinal (axially) or a combination thereof. The contact surface 148 vibrates against the skin of the patient at the target lancing site to provide pain masking sensations. In some embodiments, the vibrations may also be transferred to the piercing member 146 such that the piercing member 146 also vibrates while penetrating the skin at the target lancing site.

Figure 9:
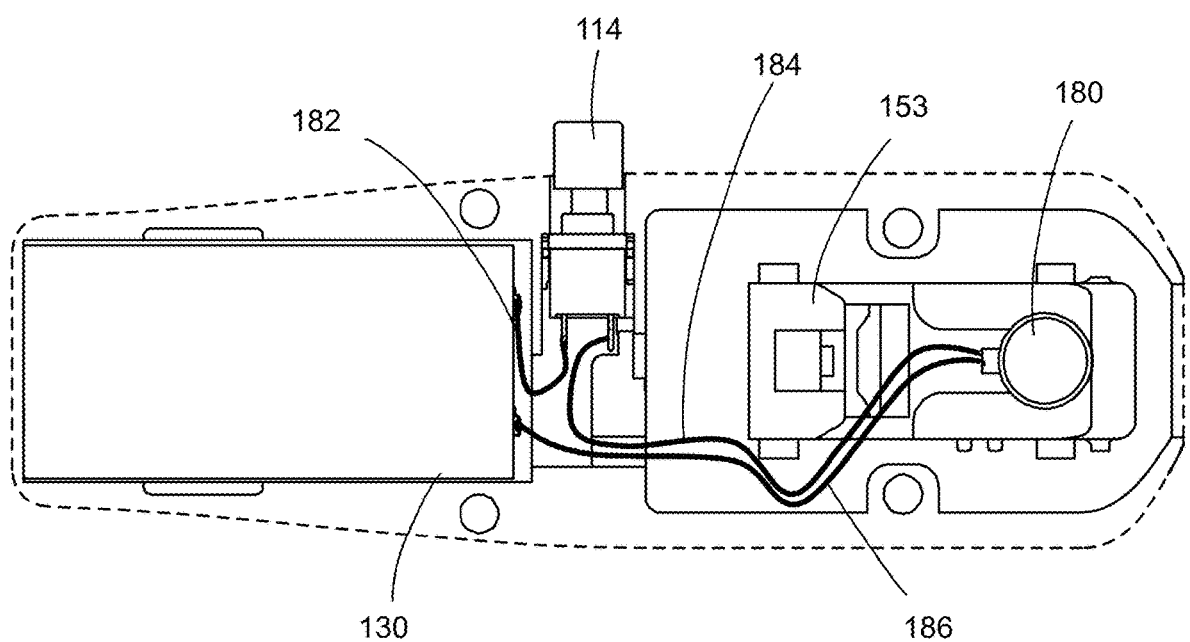
FIG. 9 is a bottom plan view of the of one embodiment of the interior of the anesthetic lancing device.

The motor 180 may be powered by a power source 130, such as shown in FIGS. 5 and 9. The power source 130 is in electrical communication with the motor 180, such as through wires 182, 184, 186 shown in FIG. 9, though other configurations are also contemplated herein. In at least one embodiment, the power source 130 is retained within the housing 110, such as a battery or batteries. Such battery may be a AAA or AA battery, a coin cell battery, 3V battery, or other similar batteries capable of providing sufficient power to operate the motor 180 and may be rechargeable or single use. In other embodiments, the power source 130 may be located externally from the housing 110 and may be connected in electrical communication with the motor 180 through wires or cables which run to and from the housing 110.

The motor 180 may be activated and deactivated through actuation of a power switch 114, such as depicted in FIGS. 1A-2B, 4 and 9. The power switch 114 may be configured to toggle the motor 180 between on and off positions, where vibrations are produced when the motor 180 is on and vibrations are not produced when the motor 180 is off. As such, the power switch 114 may be a button, knob, lever, slide bar, electronic button or other suitable structure that can be actuated by a user to turn the motor 180 on an off. The power switch 114 may therefore be accessible from the exterior of the housing 110. The power switch 114 is used to complete the electrical circuit between the power source 130 and the motor 180 such that when the power switch 114 is in the "on" position, the circuit is completed or closed and the motor 180 is on, and when the power switch 114 is in the "off" position, the circuit is open and the motor 180 is deactivated. Accordingly, the circuit may include a first wire 182 connecting the power source 130 to the switch 114, a second wire 184 connecting the switch 114 to the motor 180, and a third wire 186 connecting the motor 180 to the power source 130, as depicted in FIG. 9. In certain embodiments, the power switch 114 may not be a binary switch but rather a potentiometer providing varying degrees of electrical connectivity between the power source 130 and motor 180, such that the operation of the motor 180 may be attenuated by the amount of power supplied to it as regulated by the switch 114.

Figure 10B:
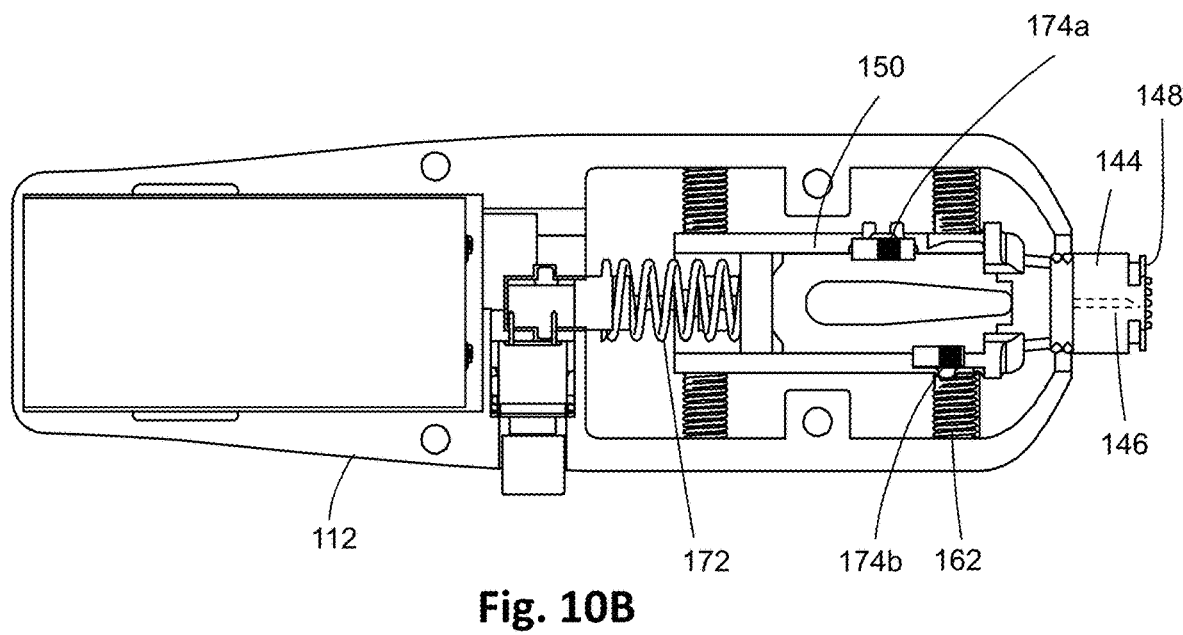
FIG. 10B is a top plan view of the exterior of the anesthetic lancing device of FIG. 10A.

To use the anesthetic lancing device 100, a user or operator inserts a disposable lancet 140 into the housing 110 with the head 144 and cap at the opening of the housing 110. Once the lancet 140 is fully seated in the carriage 150 and retained by the retention members 154, the cap of the lancet 140 may be removed from the head 144, such as by twisting off. The user may then place the device 100 against the skin of the patient, such as the heel of an infant or a fingertip of a child or adult, such that the contact surface(s) 148 are contacting the target lancing site. In some embodiments, the user may press the power switch 114 once contact is made, activating the motor 180 and producing vibrations that are transmitted to the target lancing site through the contact surface 148. In other embodiments, the user may activate the motor 180 and begin vibrating the lancet 140 prior to contact with the patient's skin. In still other embodiments, such as at least one preferred embodiment, the user may first contact the target site with the contact surface 148 of the device 100 and then begin to slightly push the device 100 against the patient until lancet 140 achieves a first position within the housing 110, which is defined as when a first force is achieved and may be detected when the first indicator 174a is visible through the first indicator window 120a on the housing top 111, as shown in FIGS. 10A-10B. Once the first position is achieved and the first indicator 174a is visible, the user may press the power switch 114 to activate the motor 180 and vibration. Regardless of when the vibration commences or how much force is applied before vibration commences, the user maintains contact of the contact surface 148 against the skin of the patient at the target site while the lancet head 144 is vibrating for a predetermined minimal period of time, such as in the range of 0.1 seconds to 1 hour, preferably at least 5-30 seconds, and more preferably about at least 10 seconds. This provides enough time in which to produce a vibration-induced anesthetic effect at the patient's skin at the incision site.

While the contact surface 148 is vibrating, and preferably upon completion of the minimal vibration-inducing anesthetic period of time, the user may continue to slightly press the device 100 further into the skin of the patient, moving the lancet 140 further into the housing 110. In some embodiments, however, the lancet 140 may continue to be advanced into the housing 110 by pressing the device 100 into the skin during the time in which the vibration-induced anesthetic effect is being accomplished. When the lancet 140 reaches a second position within the housing 110, which may be defined by when a second force is detected and determined when the second indicator 174b is visible through an indicator window 120 in the housing top 111 such as a second indicator window 120b, as shown in FIGS. 11A-11B, the lancet 140 has reached a position primed for deploying the piercing member 146. When the lancet 140 has reached this second position, the piercing member 146 may be deployed by actuating the trigger 116. Notably, vibration at the target lancing site continues during deployment of the piercing member 146 to the target lancing site. Optimally, the contact surface 148 will have been in contact with and vibrating the skin of the target site for the full vibration-induced anesthetic time, preferably at least 10 seconds, prior to actuating the trigger 116 and deploying the piercing member 146. Due to the shallow penetration depth of the piercing member 146, both the vibrating skin moving relative to piercing member 146 and the rapidly inserting and vibrating piercing member 146 will achieve similar benefits of reduction of force for penetration, less pain and trauma from incision.

Once the piercing member 146 is deployed, it is propelled through the opening 115 of the lancet 140 and into the patient's skin at the target lancing site for blood collection. It is automatically returned to the lancet body 142 and retained therein according to the internal structure of the lancet 140. The power switch 114 may again be actuated to turn the motor 180 off, halting the vibration. Standard protocol may then be followed for blood collection. The lancet may then be removed from the housing 110, such as by manually pulling the lancet 140 out through the opening in the housing 110. The retention members 154 of the carriage 150 are sufficiently resilient that they will flex and allow the lancet 140 to be removed upon manual force. The device 100 may also include a release button (not shown) that may be activated from the exterior of the housing 110 that will eject the lancet 140 from the carriage 150 and/or housing 110 when pressed.

EXAMPLES

The following examples demonstrate the feasibility of the anesthetic lancing device 100 of the present invention to reduce behavioral and neural responses to heel stick pain.

Example 1: Glucose and Metabolic Screening

Ten (10) neonatal patients (35-38 weeks' GA at birth) were enrolled into an IRB-approved crossover study. Each subject underwent two (2) heel sticks, one (1) with the anesthetic lancing device 100 of the present invention (with 15-second pre-lance vibration) (denoted as BGS in FIGS. 12A and 12B) and one with a standard of care lancet (Gentleheel®, Cardinal Health, Dublin, Ohio; non-vibrated) (denoted as Control in FIGS. 12A and 12B) in random order. Due to hospital discharge prior to the second lance, two (2) of the ten (10) subjects only underwent a single heel stick for a total of eighteen (18) heel sticks for analysis (n=3-5 scores/treatment/screening type). Skin conductance (SC), a measure of sympathetic nervous system (SNS) activation, can be monitored by electrodermal responses (ER) and is commonly reported as a rate of EDRs/sec. In this study, SC responses (# EDRs/sec) were assessed pre-lance ("Pre"), immediately following lance ("Pain"), and up to ten minutes post-lance ("Post").

Figure 12A:
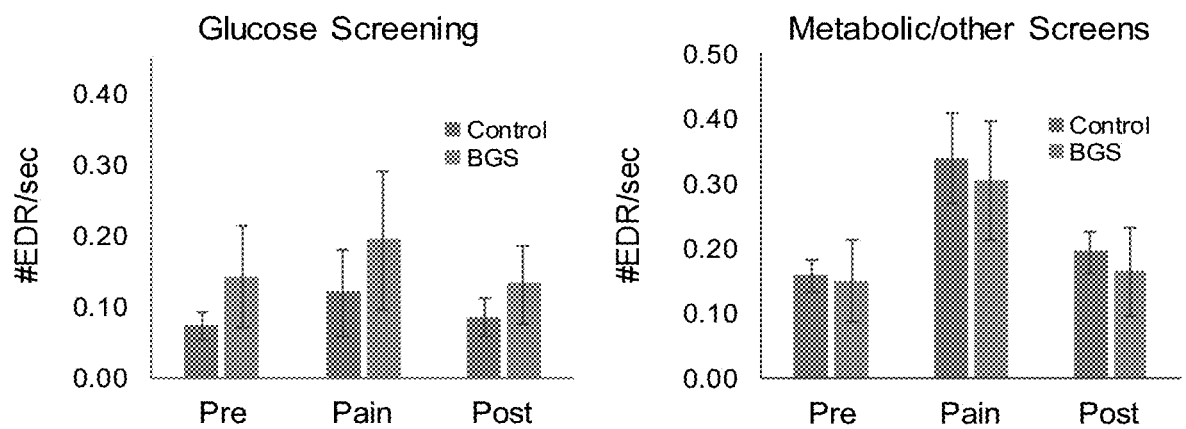
FIG. 12A are graphical data of mean SC activity during glucose screening (left) and metabolic/other screening (right) from Example 1.
Figure 12B:
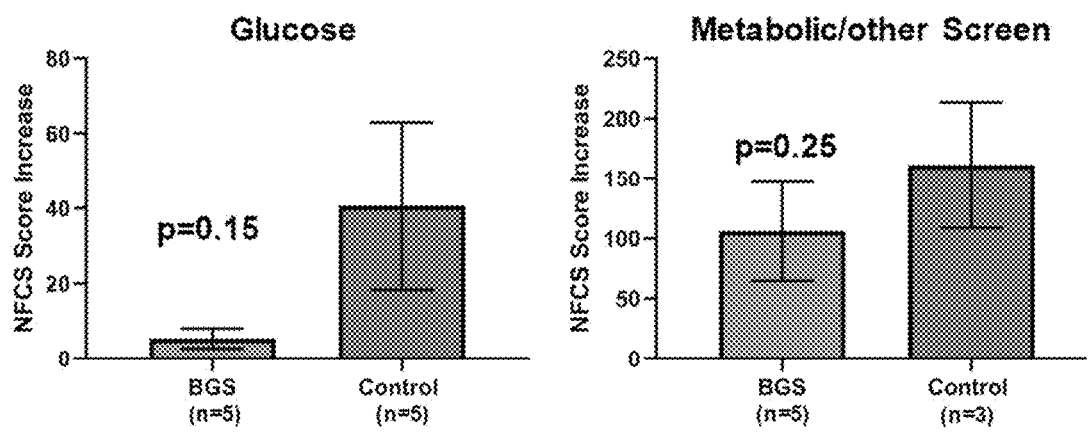
FIG. 12B are graphical data of NFCS scores for glucose screening (left) and metabolic/other screening (right) in neonatal patients from Example 1, comparing the present anesthetic lancing device to control.

The results shown in FIG. 12A indicate that SC activity was modulated by the heel lance stimulus in both treatment groups, though less so when using the anesthetic lancing device 100 of the present invention. Shifts in activity from Pre to Pain phase were greater with metabolic screening likely due to need to squeeze the heel following lance in order to obtain a greater volume of blood as compared to glucose screening, which requires a smaller collection volume. However, due to the small sample size, and small subgroup sizes (n=3-4), the results of the SC data were not statistically relevant, either in terms of # EDRs/second or mean EDR peak amplitudes. However, feasibility of SC measurements and lower sympathetic activity with the anesthetic lancing device 100 of the present invention versus a standard lancet was demonstrated on principle. Additional testing will be performed to confirm statistical relevance.

Facial actions were also video recorded for later behavioral scoring and analysis according to the Neonatal Facial Coding System (NFCS), a validated and widely accepted behavioral coding scale with high inter-rater reliability (0.84 to 1.0088) which assesses ten facial actions that are stereotypical of a neonate's reaction to noxious stimuli: brow bulge, eye squeeze, nasolabial furrow, open lips, horizontal mouth stretch, vertical mouth stretch, taut tongue, lip purse, chin quiver, and tongue protrusion. Two independent coders performed the NFCS assessment (inter-rater reliability of >85%). To ensure coders were blinded to treatment condition, the video camera focused on infant face and upper body only and the audio was on mute. Analysis of mean NFCS scores demonstrated a non-significant but lowered NFCS score with both screening types (Glucose and Metabolic/ other) when using the anesthetic lancing device 100 of the present invention with respect to lower heel stick behavioral responses, shown in FIG. 12B. This was particularly notable heel sticks for glucose screening (p=0.15). Glucose screens only require a small volume of blood, in the range of about 1-5 μL, with minimal heel squeezing/manipulation needed, thus differentiation of behavioral responses may be more genuinely attributed to the lancing event. Individual baseline NFCS score was subtracted from score at peak during heel squeezing to calculate data in either representation.

Example 2: Cortical Pain Activity

Figure 13A:
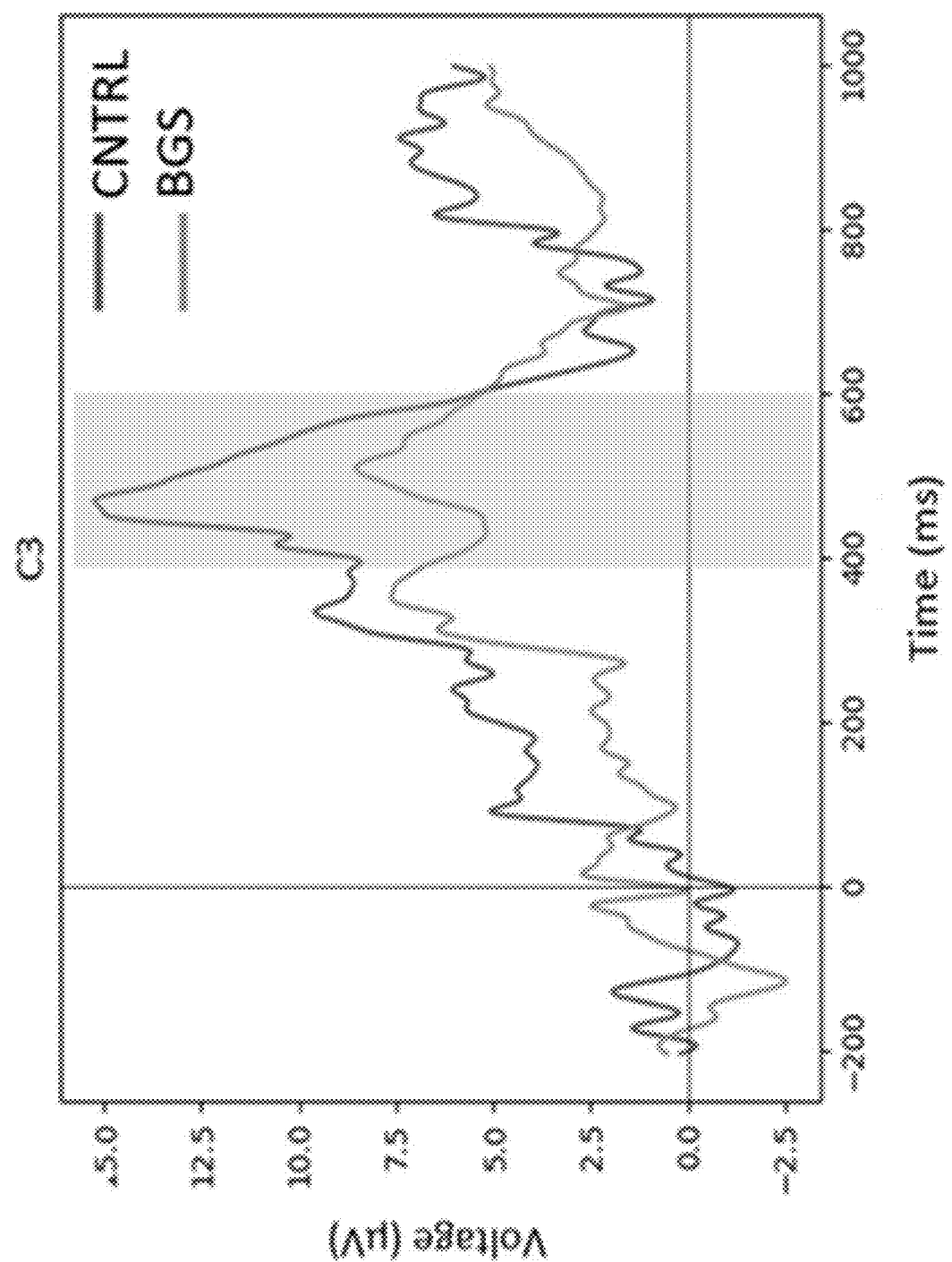
FIG. 13A are graphical preliminary data of average electroencephalogram (EEG) signals from the pilot study in Example 2 synchronized to lance across subjects by treatment, comparing the present anesthetic lancing device to control.

A pilot neonatal IRB-approved clinical trial investigating cortical pain signal (measured via EEG) for heel sticks was conducted. Subjects (N=20, n=10/treatment) were enrolled and randomized to either the anesthetic lancing device 100 of the present invention (10 sec pre-lance vibration) (denoted as BGS in FIGS. 13A-14) or a control (same lancet; no vibration applied) (denoted as Control in FIGS. 13A-14). EEG data was gathered via electrodes placed onto the C3 and CP3 areas of the brain to collect electrical brain responses specific to heel lances. EEG signals recorded within 1000 ms following the heel lance were analyzed and are shown in FIG. 13A. The area under the curve was calculated using the integrated signal amplitude in the pre-specified 400-600 ms time window after the stimulus, which corresponded to the nociceptive specific activity. Topographic EEG data was also derived were derived using Cartool freeware and analyzed using aggregate data from each group to better inform the respective layout of the brain response to heel sticks with either device.

Figure 13B:
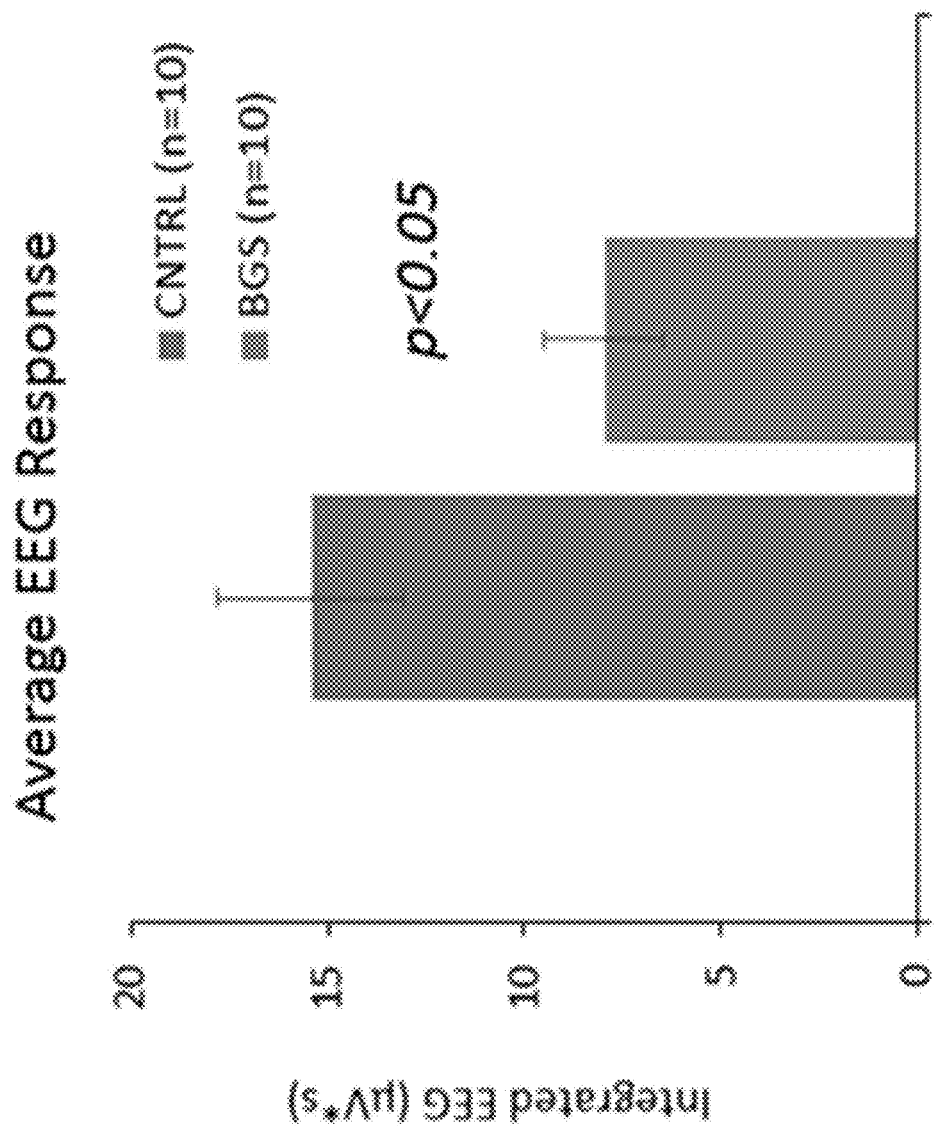
FIG. 13B are graphical preliminary data of the mean of the area under the curves of FIG. 13A.
Figure 14:
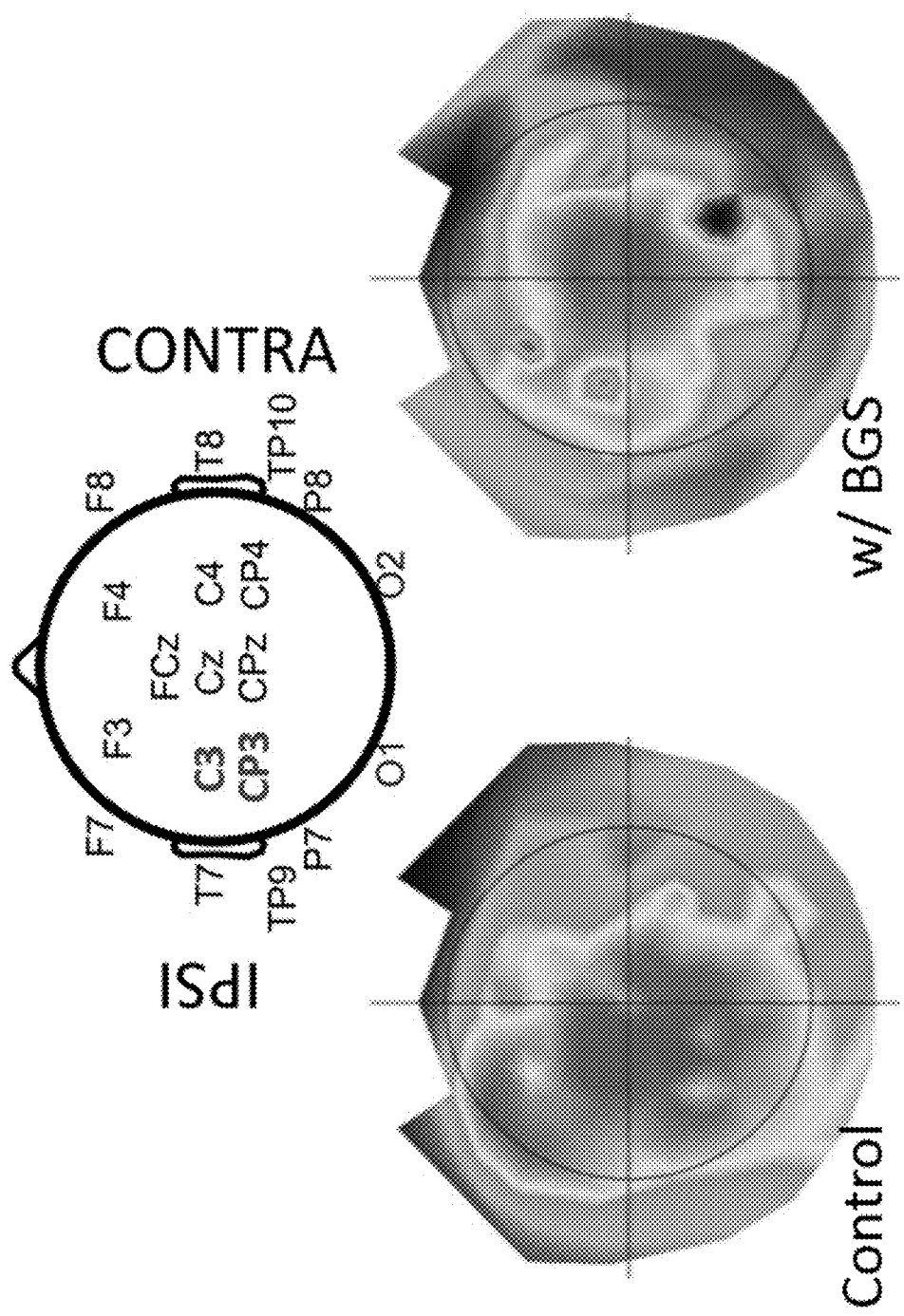
FIG. 14 are heat maps of preliminary aggregate topographic EEG data for control (left) and the present anesthetic lancing device (right) suggesting different brain responses between treatments.

The results suggest a statistically significant reduction in EEG responses between the present anesthetic lancing device 100 and the control (p=0.016, effect size=1.188), as shown in FIG. 13B. The topographic map of the brain showed that with a standard lancet, almost the entire ipsilateral hemisphere of the brain and portions of the contralateral hemisphere were activated in response to the lance, as shown in FIG. 14. With the present anesthetic lancing device 100, however, a limited response concentrated more centrally was activated in response to the lance. EEG responses were detected in the short 1-second window following the lance, the magnitude of which was dependent on treatment, firmly demonstrating feasibility of the present anesthetic lancing device 100 to reduce the cortical pain signal. The topography data of FIG. 14 suggests that the present anesthetic lancing device 100 not only reduced the magnitude of signal but produced a different pattern of activity.

Since many modifications, variations and changes in detail can be made to the described preferred embodiments, it is intended that all matters in the foregoing description and shown in the accompanying drawings be interpreted as illustrative and not in a limiting sense. Thus, the scope of the invention should be determined by the appended claims and their legal equivalents. Now that the invention has been described,

What is claimed is:

1. A lancing device, comprising:
    a housing having a first end and opposite second end, said first end including an opening dimensioned to receive a lancet therein;
    said lancet having a body, a head and a piercing member mounted within said head and selectively deployable to lance a target lancing site, said lancet removably insertable within said housing;
    a motor selectively actuated to generate vibrations;
    a contact surface disposed proximate to said piercing member on an exterior surface of at least one of said first end of said housing and said head of said lancet, said contact surface in mechanical communication with said motor and configured to:
        (i) contact said target lancing site;
        (ii) receive said vibrations from said motor; and
        (iii) transfer said vibrations to said target lancing site before deploying said piercing member and during deployment of said piercing member;
    a carriage movably suspended within said housing, said carriage configured to receive and retain said body of said lancet; and
    a plurality of isolation members disposed substantially transverse to a longitudinal axis of said lancet and biasing said carriage against said housing.

2. The lancing device as recited in claim 1, wherein said contact surface is disposed at least partially surrounding said piercing member.

3. The lancing device as recited in claim 1, further comprising a force indicating system which detects an amount of force applied to said lancet from contact with the patient's skin and indicate to the user when at least one of: (i) a first force applied to said lancet has been achieved to begin vibration producing an anesthetizing effect and (ii) a second force applied to said lancet has been achieved to trigger said lancet for piercing to a predetermined depth will be reached, wherein said force indicating system further comprises:
    (iii) a force sensor in communication with said lancet and configured to detect said force applied to said lancet; and
    (iv) at least one indicator perceptible to a user during operation and configured to provide information indicative of at least one of said first and second forces applied to said lancet.

4. The lancing device as recited in claim 3, wherein increased force applied to said lancet moves said lancet further within said housing.

5. The lancing device as recited in claim 3, wherein said at least one indicator further comprises a first indicator indicative of said first force applied to said lancet and detected by said force sensor and a second indicator indicative of said second force applied to said lancet and detected by said force sensor, wherein said second force is greater than said first force and said first and second indicators are configured to be sequentially presented to the user.

6. The lancing device as recited in claim 5, wherein said lancet is in a first position when said first indicator is presented to the user and in a second position when said second indicator is presented to the user, wherein a greater portion of said lancet is received within said housing in said second position.

7. The lancing device as recited in claim 3, wherein said first force corresponds to readiness to commence vibration and said second force corresponds to readiness to deploy said piercing member.

8. The lancing device as recited in claim 5, wherein said first and second indicators are viewable through an indicator window on said housing when said first or second indicator aligns with said indicator window.

9. The lancing device as recited in claim 8, wherein said first indicator is viewable through a first indicator window on said housing when said first indicator aligns with said first indicator window and said second indicator is viewable through a second indicator window on said housing when said second indicator aligns with said second indicator window.

10. The lancing device as recited in claim 1, wherein said carriage is configured to at least one of: (i) maintain alignment of said piercing member with said opening, (ii) move longitudinally within said housing toward said second end prior to deployment of said piercing member, and (iii) be movably suspended within said housing.

11. The lancing device as recited in claim 10, further comprising an alignment member affixed to said housing and configured to one of: (i) maintain alignment of said carriage within said housing relative to said opening and (ii) limit movement of the carriage along a vertical axis of the housing.

12. The lancing device as recited in claim 11, further comprising a trigger movably mounted to said housing and in communication with a lancet trigger on said lancet, wherein actuating said trigger causes said lancet trigger to be actuated and said piercing member to be deployed.

13. The lancing device as recited in claim 12, wherein actuating said trigger causes said carriage to move toward said housing and said alignment member restricts said movement of said carriage toward said housing beyond a predefined point.

14. The lancing device as recited in claim 10, wherein said carriage includes at least one guide member configured to assist in positioning of said body of said lancet in said carriage.

15. The lancing device as recited in claim 14, wherein said at least one guide member includes at least one indicator perceptible to a user during operation and configured to provide information indicative of a force applied to said lancet.

16. The lancing device as recited in claim 1, wherein said plurality of isolation members are disposed between said motor and a portion of said housing configured to be held by a user during operation, said plurality of isolation members configured to isolate vibrations from said motor to said portion of said housing.

17. The lancing device as recited in claim 16, wherein said plurality of isolation members are springs.

18. The lancing device as recited in claim 1, wherein said motor is operative to vibrate said contact surface at a frequency in the range of 50-500 Hz.

19. The lancing device as recited in claim 18, wherein said motor is operative to vibrate said contact surface at a frequency at about 150 Hz.

20. A method of using a lancing device having an anesthetic feature, said method comprising:
    inserting a lancet having a piercing member into a housing through an opening in said housing until said lancet is oriented within a carriage movably suspended within said housing and proximate to said opening,
    wherein at least one of said lancet and said housing have a contact surface on an exterior surface thereof,
    wherein a plurality of isolating members are disposed substantially traverse to a longitudinal axis of said lancet and biases said carriage against said housing;

contacting a target lancing site with said contact surface;

activating a motor in said housing to produce vibrations, vibrating said target lancing site by transferring said vibrations from said motor through said contact surface to said target lancing site;

holding said contact surface against said target lancing site while vibrating;

deploying said piercing member of said lancet to said target lancing site while maintaining vibration of said target lancing site by said contact surface.

21. The method as recited in claim 20, wherein holding said contact surface against said target lancing site while vibrating occurs for a predetermined period of time in a range of 0.1 second to 1 hour.

22. The method as recited in claim 21, wherein holding said contact surface against said target lancing site while vibrating occurs for a predetermined period of time of about 10 seconds.

23. The method as recited in claim 20, further comprising applying first and second forces to said lancet and detecting said first and second forces applied to said lancet, wherein said steps of activating said motor and deploying said piercing member are determined by said first and second forces, and wherein a force indicating system detects an amount of force applied to said lancet from contact with the patient's skin and indicates to the user when at least one of (i) said first force applied to said lancet has been achieved to begin vibration producing an anesthetizing effect and (ii) said second force applied to said lancet has been achieved to trigger said lancet for piercing to a predetermined depth will be reached.

24. The method as recited in claim 23, further comprising:

applying increasing force to said lancet, detecting said first force and said second force, wherein said second force is greater than said first force;

activating said motor to produce vibrations when said first force is detected; and deploying said piercing member of said lancet when said second force is detected;

wherein a first indicator indicates said first force being applied to said lancet and detected by a force sensor and a second indicator indicates said second force being applied to said lancet and detected by said force sensor.

25. The method as recited in claim 24, wherein said first force is in the range of about 0.001 to 10 N.

26. The method as recited in claim 25, wherein said first force is about 1 N.

27. The method as recited in claim 24, wherein said second force is in the range of about 2 to 10 N.

28. The method as recited in claim 27, wherein said second force is about 3 N.

29. The method as recited in claim 20, wherein deploying said piercing member of said lancet lances tissue at said target lancing site to a depth in the range of 2-2.5 mm and with an incision width in the range of 0.85-2 mm.

30. The method as recited in claim 29, wherein deploying said piercing member of said lancet lances tissue at said target lancing site to a depth is about 1.8 mm and with an incision width of about 1 mm.

31. The lancing device as recited in claim 1, wherein said first force sufficient to produce an anesthetizing effect is one of: (i) in the range of about 0.001 to 10 N and (ii) about 1 N.

32. The lancing device as recited in claim 1, wherein said second force sufficient to achieve said predetermined depth is one of: (i) in a range of about 2 to 10 N and (ii) about 3 N.

33. The lancing device as recited in claim 3, wherein said predetermined depth is one of: (i) in the range of 1.8 to 2.5 mm, (ii) in the range of 1.8-2 mm, and (iii) 1.8 mm.

* * * * *